United States Patent
Dellinger et al.

(10) Patent No.: US 12,421,274 B1
(45) Date of Patent: Sep. 23, 2025

(54) POLYMER BEADS FOR OLIGONUCLEOTIDE SYNTHESIS

(71) Applicant: AGILENT TECHNOLOGIES, INC., Santa Clara, CA (US)

(72) Inventors: Douglas J. Dellinger, Boulder, CO (US); Logan Garner, Boulder, CO (US); John W. Davies, Shrewsbury (GB); Thomas Jacob Cobb, Shrewsbury (GB); Richard Bacon, Church Stretton (GB); David James Neep, Church Stretton (GB); Matthew Williamson, Church Stretton (GB)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 18/905,854

(22) Filed: Oct. 3, 2024

(51) Int. Cl.
*C07H 21/00* (2006.01)
*C07H 1/00* (2006.01)
*C08F 212/08* (2006.01)
*C08F 212/12* (2006.01)
*C08F 212/36* (2006.01)

(52) U.S. Cl.
CPC ............... *C07H 21/00* (2013.01); *C07H 1/00* (2013.01); *C08F 212/08* (2013.01); *C08F 212/12* (2013.01); *C08F 212/36* (2013.01); *C08F 2810/20* (2013.01)

(58) Field of Classification Search
CPC .... C08F 212/08; C08F 212/12; C08F 212/36; C07H 21/00
See application file for complete search history.

(56) References Cited

U.S. PATENT DOCUMENTS

| | | | |
|---|---|---|---|
| 4,459,378 A | 7/1984 | Ugelstad | |
| 5,391,667 A | 2/1995 | Dellinger | |
| 8,592,542 B2 | 11/2013 | Mori et al. | |
| 8,653,152 B2 | 2/2014 | Mori et al. | |
| 11,814,450 B2 | 11/2023 | Song et al. | |
| 2024/0010774 A1 | 1/2024 | Wang et al. | |

FOREIGN PATENT DOCUMENTS

| WO | 2006/077406 A1 | 7/2006 |
| WO | 2022/110559 A1 | 6/2022 |

OTHER PUBLICATIONS

Letsinger et al., Journal of the American Chemical Society, 1964, 86(23), p. 5163-5165. (Year: 1964).*
Immergut, E.H., Die Makromolekulare Chemie, 1953, 10(1), p. 93-106. (Year: 1953).*
Tang, Yuan-hui et al. Advanced Membranes, vol. 2, 2022, 100033, ISSN 2772-8234.

* cited by examiner

*Primary Examiner* — Jonathan S Lau
(74) *Attorney, Agent, or Firm* — Lando & Anastasi, LLP

(57) ABSTRACT

A resin formed of copolymer beads is disclosed. The copolymer beads have a first repeating motif, a second repeating motif having a substituted styrene with an ester functional group or an amide with a terminal amine or hydroxyl functional group, and a crosslinking agent having a divinyl compound. The copolymer beads are capable of expanding substantially uniformly in polar and non-polar solvents.

18 Claims, 12 Drawing Sheets

Synthesis and functionalization of copolymer bead

Comparison of particle swelling in polar and non-polar solvents
(A) Particle swelling pre-surface functionalization.

Comparison of particle swelling in polar and non-polar solvents.
(B) Particle swelling post-amination with ethylenediamine (EDA)

Particle diameter size distribution across bead population

Particle diameter size distribution across population of beads made by suspension polymerization Conversion of ester groups (beads of formula (I)) to amine or hydroxyl groups (beads of formula (II))

Conversion of ester groups (beads of formula (I)) to amine or hydroxyl groups (beads of formula (III))

Bead of formula (II) loading with nucleoside through a succinate linker

Bead of formula (II) loading with nucleoside through a succinate linker dT amidite Bead of formula (III) loading with nucleoside through a succinate linker Representative LC trace corresponding to LC/MS analysis of crude oligonucleotide synthesis products.

POLYMER BEADS FOR OLIGONUCLEOTIDE SYNTHESIS

FIELD OF TECHNOLOGY

Aspects and embodiments disclosed herein generally relate to polymer beads for oligonucleotide synthesis, and more specifically, to polymer beads that are compatible with polar and non-polar solvents.

SUMMARY

In accordance with one aspect, there is provided a copolymer bead comprising a first repeating motif, a second repeating motif having a substituted styrene of formula (I), and a crosslinking agent comprising a divinyl compound,

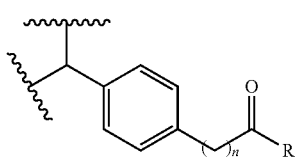

(I)

wherein n is an integer between 0 and 12; R is O—$R^1$ or NH—$R^2$-Q; $R^1$ is a $C_1$-$C_6$ alkyl, a $C_1$-$C_6$ substituted alkyl, a $C_6$-$C_{12}$ aryl or a $C_6$-$C_{12}$ substituted aryl; $R^2$ is a $C_1$-$C_{36}$ alkyl or a $C_1$-$C_{36}$ substituted alkyl, and Q is $NH_2$ or OH.

In some embodiments, the first repeating motif comprises a styrene.

In some embodiments, the second repeating motif is a substituted styrene of formula (I), wherein n is 0 or 1 and $R^1$ is methyl.

In some embodiments, the second repeating motif is a compound of one of formulas (II) or (III):

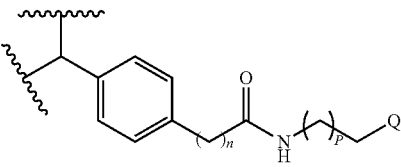

(II)

wherein Q is $NH_2$ or OH, n is an integer from 0 to 12, and p is an integer from 0 to 11;

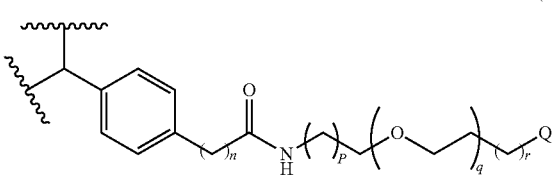

(III)

wherein Q is $NH_2$ or OH, n is an integer from 0 to 12, p and r are integers each independently from 0 to 11, and q is an integer from 0 to 6.

In some embodiments, the divinyl compound comprises divinylbenzene or ethylene glycol di(meth)acrylate.

In some embodiments, the copolymer bead has a bead diameter between 30 and 200 μm.

In some embodiments, the copolymer bead has a bead diameter between 50 and 90 μm.

In some embodiments, the second repeating motif further comprises at least one of a cleavable linker, a nucleoside or nucleoside derivative.

In some embodiments, the second repeating motif further comprises a nucleoside derivative and is represented by formula (IV):

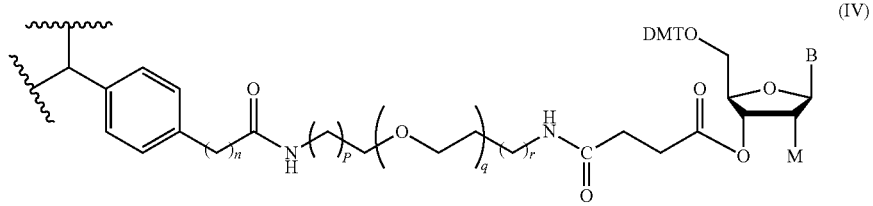

(IV)

wherein n is 0 or 1; p is 1-6; q is 0-3; r is 1-6; B is a nucleobase, a protected nucleobase, a nucleobase analog, or a protected nucleobase analog; M is H, a protected hydroxyl, O-alkyl, 2-methoxyethanolate (MOE), F, or a methylene linked to C4' of the ribose.

In some embodiments, the second repeating motif further comprises a cleavable linker and is represented by formula (V):

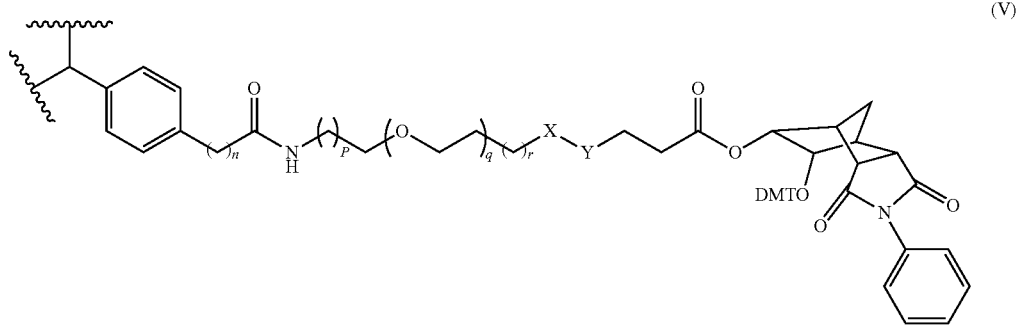

wherein n is 0 or 1, p is 1-6, q is 0-3, r is 1-6, X is NH or O, and Y is C=O.

In some embodiments, the copolymer bead has a porous structure.

In accordance with another aspect, there is provided a resin formed of copolymer beads comprising a first repeating motif, a second repeating motif having a substituted styrene with an ester functional group or an amide with a terminal amine or hydroxyl functional group, and a crosslinking agent comprising a divinyl compound, the copolymer beads being capable of expanding substantially uniformly in polar and non-polar solvents.

In some embodiments, the second repeating motif comprises a substituted styrene of formula (I),

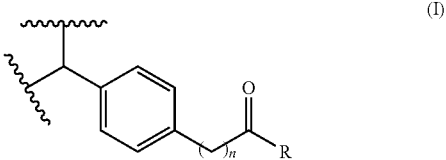

wherein n is an integer between 0 and 12; R is O—R¹ or NH—R²-Q; R¹ is a $C_1$-$C_6$ alkyl, a $C_1$-$C_6$ substituted alkyl, a $C_6$-$C_{12}$ aryl or a $C_6$-$C_{12}$ substituted aryl; R² is a $C_1$-$C_{36}$ alkyl or a $C_1$-$C_{36}$ substituted alkyl, and Q is $NH_2$ or OH.

In some embodiments, the first repeating motif comprises a styrene.

In some embodiments, the divinyl compound comprises divinylbenzene, ethylene glycol di(meth)acrylate, or a combination thereof.

In some embodiments, the copolymer beads expand to a predetermined volume of less than 3 times their dry volume.

In some embodiments, the predetermined volume is from about 2 to about 3 times their dry volume.

In some embodiments, the copolymer beads have an average bead diameter between 30 and 200 μm.

In some embodiments, the copolymer beads have an average bead diameter between 50 and 90 μm.

In accordance with another aspect, there is provided an emulsion comprising a continuous phase and a dispersed phase. The continuous phase may comprise a solvent. The dispersed phase may comprise a first monomer; a second monomer comprising a substituted styrene of formula (I-A); a crosslinking agent comprising a divinyl compound; and an effective amount of a diluent to produce a copolymer bead having a target porosity and surface area when the copolymer bead is expanded,

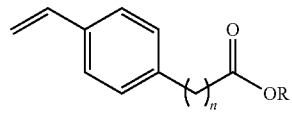

wherein n is an integer between 0 and 12, and R is a $C_1$-$C_6$ alkyl, a substituted alkyl, a phenyl or a substituted phenyl.

In some embodiments, the diluent comprises toluene, isopropyl alcohol, diethylbenzene, ethyl acetate, cyclohexanone, or a combination thereof.

In some embodiments, the effective amount of the diluent is from about 60 vol % to about 75 vol %.

In some embodiments, the emulsion comprises from about 7 vol % to about 16 vol % of the crosslinking agent.

In some embodiments, the emulsion comprises from about 2 vol % to about 30 vol % of each of the first and second monomer.

In some embodiments, an amount of the first monomer is about 1× to 10× an amount of the second monomer.

In accordance with another aspect, there is provided a method of facilitating oligonucleotide synthesis. The method may comprise providing a resin formed of copolymer beads comprising a first repeating motif, a second repeating motif having a substituted styrene with an ester functional group or an amide with a terminal amine or hydroxyl functional group, and a crosslinking agent comprising a divinyl compound, the copolymer beads being capable of expanding substantially uniformly in polar and non-polar solvents. The method may comprise providing instructions to combine the resin with an effective amount of a solution comprising protected nucleosides, protected nucleoside analogs, or derivatives thereof to couple at least one protected nucleoside or protected nucleoside analog to a plurality of the copolymer beads.

In some embodiments, the second repeating motif comprises a substituted styrene of formula (I),

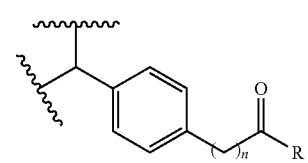

wherein n is an integer between 0 and 12; R is O—$R^1$ or NH—$R^2$-Q; $R^1$ is a $C_1$-$C_6$ alkyl, a $C_1$-$C_6$ substituted alkyl, a $C_6$-$C_{12}$ aryl or a $C_6$-$C_{12}$ substituted aryl; $R^2$ is a $C_1$-$C_{36}$ alkyl or a $C_1$-$C_{36}$ substituted alkyl, and Q is $NH_2$ or OH.

In some embodiments, the first repeating motif comprises a styrene and the divinyl compound comprises divinylbenzene, ethylene glycol di(meth)acrylate, or a combination thereof.

In some embodiments, the method comprises providing the resin in dry powder form.

In some embodiments, the method comprises providing the resin in solvated or expanded form.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
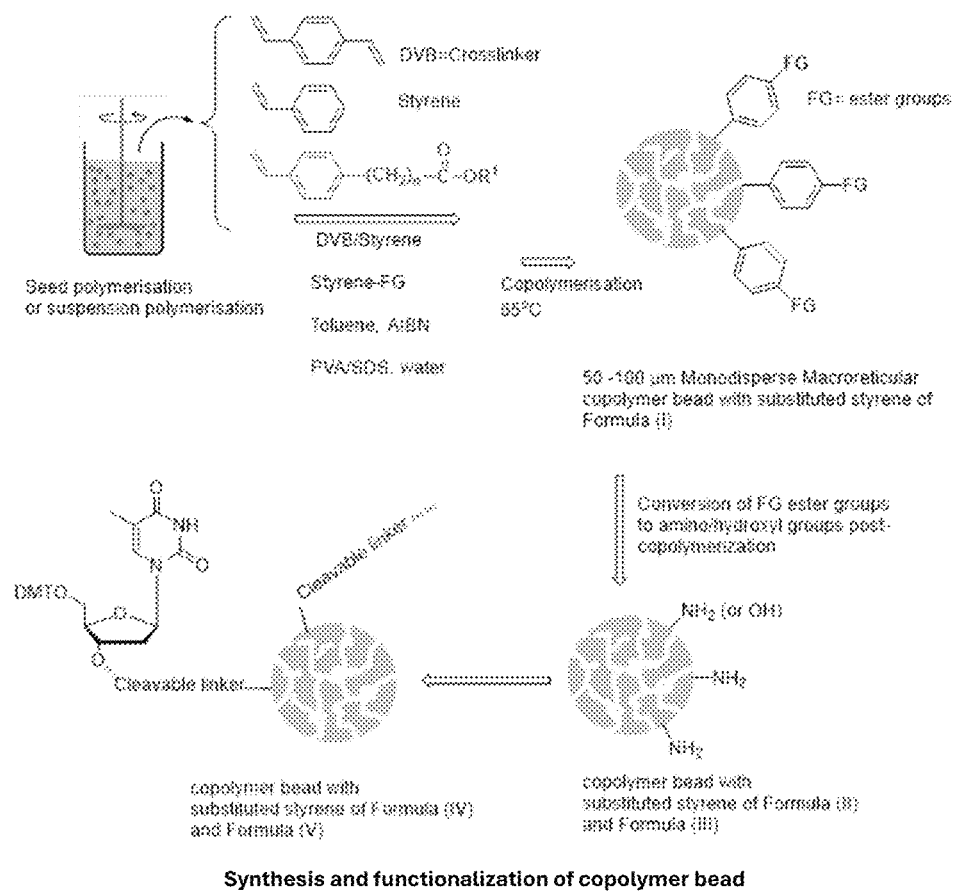
FIG. 1 is a schematic diagram showing synthesis and functionalization of a copolymer bead, according to one embodiment.

Oligonucleotide synthesis is the chemical process by which individual nucleotides are sequentially linked to form a desired structure. Often, oligonucleotide synthesis is performed on a solid phase substrate. A starting molecule may be tethered to the solid phase substrate to begin the synthesis. At least one site may be available on the starting molecule to bind a first nucleotide. The synthesis may proceed by sequentially binding nucleotides until the oligonucleotide is produced and then finally cleaved from the solid phase substrate.

A column, such as a fixed bed column, may be loaded with the solid phase substrate. Use of the solid phase may facilitate synthesis cycle protocols which utilize a large excess of reagents to improve coupling efficiencies, and further facilitate the removal of such reagents and biproducts prior to proceeding to the next step in the protocol. The composition and structure of the solid phase is believed to have a significant effect on the efficiency, yield, purity, and achievable length of the desired product.

The reagents and solvents used during an oligonucleotide synthesis protocol may vary from highly polar to highly non-polar. Initially, inorganic insoluble materials, such as glass or silica, were used to produce the solid phase substrate. Inorganic insoluble solid phase beads tend to be rigid, and their shapes, sizes, and surface areas are generally unaffected by the different reagents and solvents used during the synthesis protocols. However, inorganic insoluble solid phase beads have limited capacity for loading.

The demand for large-scale oligonucleotide synthesis has grown with the development and approval of oligonucleotide therapeutic agents. To satisfy the growing demand for oligonucleotide agents, organic polymer solid phase substrates have been developed. Organic polymer beads tend to swell and shrink in response to the different reagents and solvents utilized during oligonucleotide synthesis protocols. When swollen, the organic polymers may allow for a greater surface area of the solid phase matrices to be utilized for attachment and growth of the oligonucleotide, and thus may allow for the production of greater quantities of oligonucleotide per volume of solid phase substrate. However, when the organic polymer beads come into contact with a shrinking reagent, the rate of production is limited by the reduced size of the substrate.

Thus, there is a need for a solid phase substrate that expands more consistently over a larger variety of reagents and solvents. The polymer beads disclosed herein surprisingly maintain more consistent expansion across a range of solvents and solvent polarities. For instance, the polymer beads were surprisingly found to expand almost equally in polar and non-polar solvents. The polymer beads disclosed herein may also contain pores. Upon expansion, the porous structure may provide an even larger surface area for oligonucleotide synthesis. The ability to expand consistently across different solutions and provide a larger surface area for attachment increases the amount of oligonucleotide produced per volume of solid phase substrate, which in turn reduces the amount of solid phase substrate necessary to produce a desired quantity of product.

While not wishing to be bound by theory, it is believed that certain factors have an effect on the ability of the polymer bead to expand substantially uniformly in different reagents, such as in polar and non-polar solvents. These factors may include, for example, one or more of the amount and degree of crosslinking, the nature of the crosslinker, and the amount and type of diluent used during polymerization of the bead. The amount and type of diluent is believed to have an effect on the pore structure of the polymer beads, including, for example, pore size, pore volume, porosity, and surface area.

Furthermore, the polymer beads disclosed herein may be provided with a substantially monodispersed size distribution, which is a narrower distribution than conventionally produced solid phase substrates. While not wishing to be bound by theory, it is believed that beads having a substantially monodispersed size distribution are able to produce a batch of oligonucleotide product having a higher percent purity. For instance, beads having a more monodispersed size distribution are believed to reduce error probability in the synthesis process. It is believed that a more monodispersed size distribution provides better flow characteristics through the column. The reagents and solvents are able to more evenly distribute throughout a column loaded with beads having a substantially monodispersed size distribution, improving diffusion and producing a more consistent product. The uniformity of the packed bed may reduce the amount of nucleosides, solvents or reagents, and other materials needed to produce a desired quantity of product. Accordingly, the organic polymer solid phase substrate disclosed herein may be able to increase the amount of oligonucleotides produced, while reducing the cost of production per oligonucleotide.

The disclosure relates generally to polymer beads utilized as solid phase substrates for the synthesis of oligonucleotides. However, it should be noted that in certain embodiments the polymer beads may be utilized for synthesis of other biologically active agents, such as polymers, peptides, oligosaccharides, and others.

Polymers are typically made by a series of reactions, often stepwise, in which a first monomer is covalently attached to a second monomer, which in turn is then covalently attached to a third monomer, to form a growing polymer in a process known as polymerization. Once attached, the monomers become repeating motifs that make up the polymer structure. A copolymer is a polymer formed by the combination of two or more different repeating motifs.

In accordance with one aspect, there is provided a polymer bead formed of a copolymer having a first hydrophobic repeating motif and a second repeating motif that confers some hydrophilicity on the surface of the finished polymer. The polymer bead may also be referred to as a copolymer bead herein.

The copolymer bead may include one or more functionalized repeating motifs and one or more crosslinking agents. In certain embodiments, the bead may be formed by copolymerizing at least a first aromatic monovinyl compound with at least a second aromatic monovinyl compound having a functional group and one or more divinyl compound for crosslinking, where the functional group is one or more functional group that does not become involved in the polymerization.

The aromatic monovinyl compound may be selected to be immiscible with water and capable of copolymerizing with a divinyl compound, such as divinyl benzene. One exemplary aromatic monovinyl compound is styrene. Other exemplary aromatic monovinyl compounds include methyl methacrylate, vinyl toluene, alpha methyl styrene, ethyl vinyl ether, ethyl vinyl benzene, etc., and isomers thereof.

The functionalized repeating motif may be a substituted styrene having the functional group. In certain embodiments, the styrene may be substituted at the para position. In other embodiments, the styrene may be substituted at the meta or ortho positions. The functional group may be selected to be capable of reacting with an amine. Exemplary functional groups include ester groups and amides having a terminal amine or hydroxyl functional group. Other exemplary functional groups include terminal halogens (e.g., fluorine, chlorine, bromine, or iodine). One exemplary functionalized repeating motif is a para-substituted styrene having an ester group.

In certain embodiments, the functionalized repeating motif may be a compound of formula (I):

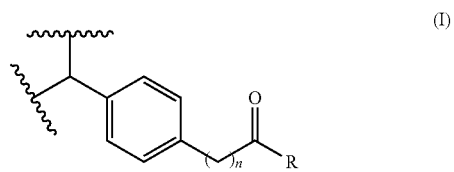

wherein n is an integer between 0 and 12; R is O—$R^1$ or NH—$R^2$-Q; $R^1$ is a $C_1$-$C_6$ alkyl, a $C_1$-$C_6$ substituted alkyl, a $C_6$-$C_{12}$ aryl or a $C_6$-$C_{12}$ substituted aryl; $R^2$ is a $C_1$-$C_{36}$ alkyl or a $C_1$-$C_{36}$ substituted alkyl, and Q is $NH_2$ or OH.

As disclosed herein, a wavy line projected from a substituent, such as:

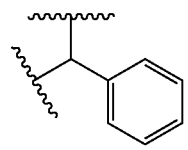 [SMILES: *C(*)c1ccccc1]

may indicate a covalent bond site of a repeating motif, beyond which is a polymerization site of an adjacent moiety, such as an adjacent repeating motif.

The term alkyl may refer to monovalent saturated aliphatic hydrocarbyl groups having a plurality of carbon atoms, e.g., 1 to 36 carbon atoms or more. This term may include, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

A substituted alkyl may refer to an alkyl group having substituents, e.g., 1 to 5, 1 to 3, 1 to 2, or more substituents. Exemplary substituents include alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio.

The term aryl may refer to a monovalent aromatic carbocyclic group of carbon atoms, e.g., 6 to 14 or more carbon atoms, having a single ring (e.g., phenyl) or multiple condensed rings (e.g., naphthyl or anthryl). In general, the condensed rings may or may not be aromatic (e.g., 2-benzoxazolinone, 2H-1,4-benzoxazin-3(4H)-one-7-yl, and the like) provided that the point of attachment is at an aromatic carbon atom. Exemplary aryl groups may include phenyl and naphthyl.

A substituted aryl may refer to aryl groups which are substituted with a plurality of substituents, e.g., 1 to 5, 1 to 3, 1 to 2 or more substituents. Exemplary substituents are selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio.

It is understood that the compounds described herein are not intended to include impermissible substitution patterns. Such impermissible substitution patterns are well known to the skilled artisan. Exemplary substituents are described in the Appendix.

In certain exemplary embodiments, the functionalized repeating motif may be a compound of formula (I), wherein n is 0 or 1 and $R^1$ is methyl. One exemplary functionalized repeating motif is a compound of formula (I-A):

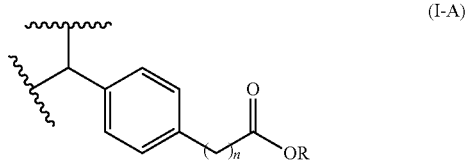

(I-A)

wherein n is an integer between 0 and 12, and R is a $C_1$-$C_6$ alkyl, a substituted alkyl, a phenyl or a substituted phenyl. One exemplary compound of formula (I-A) is methyl 2-(4-vinylphenyl)acetate.

In some embodiments, the functional group may be an amide having a terminal hydroxyl or amine functional group. When polymerized, amides are generally more hydrophilic than ester functional groups. Conversely, ester groups are generally more hydrophobic than amides. In some embodiments, the ester group may be converted to an amide. Thus, conversion of the ester group to an amide may generally provide a copolymer having a more hydrophilic repeating motif, in addition to providing a functional terminal group to anchor a nucleoside, nucleoside analog, or nucleoside derivate or cleavable linker.

One method of converting an ester functional group to an amide is by reacting the monomer or copolymer having the repeating motif with diamine or amine alcohol to form the amide having a terminal amine (diamine) or a terminal hydroxyl (amine alcohol). An ester group may be converted to an amide before polymerization into the copolymer bead or after polymerization into the copolymer bead. In some embodiments, at least 90% of the ester functional groups of the copolymer are converted to amides, for example, at least 95%, at least 98%, at least 99%, at least 99.9%, or at least 99.99%.

Exemplary substituted styrene repeating motifs having an amide with a terminal amine or hydroxyl functional group include compounds of one formula (II) or (III):

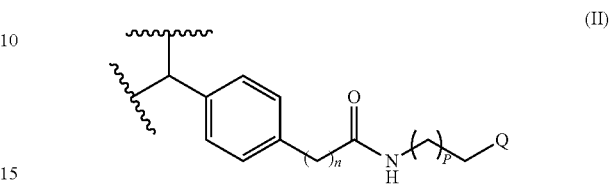

(II)

wherein Q is $NH_2$ or OH, n is an integer from 0 to 12, and p is an integer from 0 to 11;

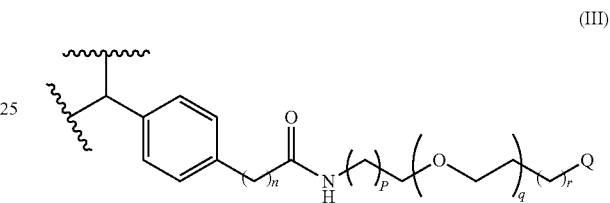

(III)

wherein Q is $NH_2$ or OH, n is an integer from 0 to 12, p and r are integers each independently from 0 to 11, and q is an integer from 0 to 6.

The compounds of formula (II) and (III) may be formed by converting an ester group of the compound of formula (I-A) to an amide group. Alternatively, the compounds of formula (II) or (III) may be formed by any suitable method.

In certain embodiments, the functionalized repeating motif may be 4-vinylbenzyl chloride, 4-ethynyl-benzeneacetic ester, or methyl-4-vinylbenzoate. Other exemplary functionalized repeating motifs include methacrylates having the functional group. The methacrylate functionalized repeating motif may comprise, for example, methyl methacrylate, ethyl methacrylate, 4-nitrophenyl methacrylate, etc.

In some embodiments, the functionalized repeating motif may further comprise a cleavable linker. Linkers generally provide a connection between two compounds that can be cleaved upon exposure to a trigger, such as a chemical agent, UV light exposure, an enzyme or a combination of different agents.

In some embodiments, the term linker may refer to a single covalent bond or a series of stable covalent bonds incorporating 1-20 nonhydrogen atoms selected from the group consisting of C, N, O, S and P that covalently attach the repeating motif compounds to another moiety such as a chemically reactive group or a biological or non-biological component, e.g., a nucleoside or nucleoside analog. Exemplary linking members include a moiety that includes —C(O)NH—, —C(O)O—, —NH—, —S—, —O—, and the like.

A cleavable linker may refer to a linker that has one or more cleavable groups that may be broken by the result of a reaction or condition. A cleavable group generally refers to a moiety that allows for release of a portion, e.g., a nucleoside or nucleoside analog moiety, of a conjugate from the remainder of the conjugate by cleaving a bond linking the released moiety to the remainder of the conjugate. Such cleavage may be chemically triggered, enzymatically triggered, or triggered by ultraviolet (UV) light exposure.

The functionalized repeating motif may comprise a linker designed to facilitate oligonucleotide synthesis. For instance, the linker may anchor a first nucleoside to the bead, and be cleaved after completion of synthesis for release of the oligonucleotide. Exemplary linkers include succinate linkers, universal linkers (UnyLinker), phosphate linkers that contain a cleavable unit for example a succinate spacer, photocleavable linkers, such as nitrobenzyl containing linkers, or enzymatically cleavable linkers, such as peptides cleavable by a protease.

One exemplary repeating motif having a cleavable linker is represented by the compound of formula (III-A):

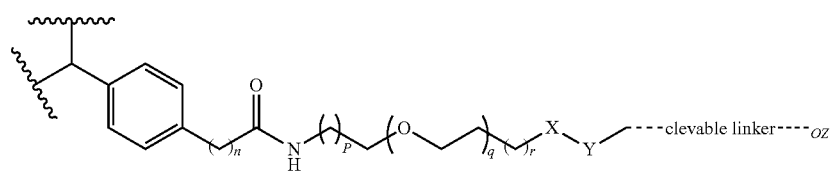

(III-A)

wherein n is an integer from 0 to 12, p and r are integers each independently from 0 to 11, q is an integer from 0 to 6, X is O or NH; when X is O, Y is C=O, $PO_2$, or $NC-(CH_2-CH_2)-O-P(=O)$, and when X is NH, Y is C=O; and Z is H or 4,4-dimethoxytrityl (DMT).

Another exemplary repeating motif having a cleavable linker is represented by the compound of formula (V):

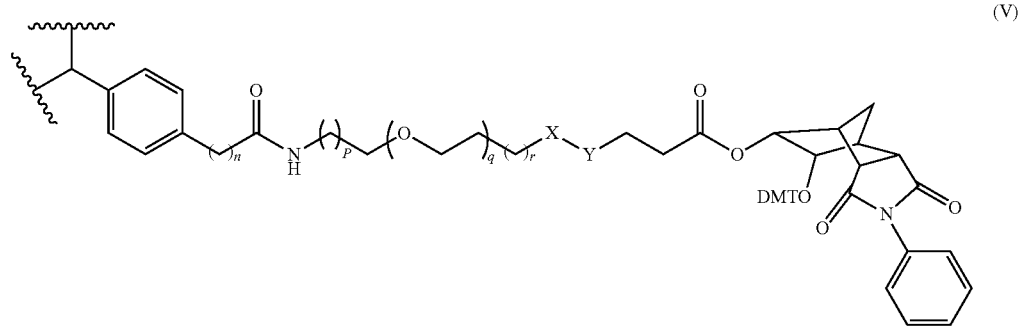

(V)

wherein n is 0 or 1, p is 1-6, q is 0-3, r is 1-6, X is NH or O, and Y is C=O.

The copolymer bead may comprise a crosslinking agent. One exemplary crosslinking agent is a divinyl compound. Exemplary divinyl compounds include divinylbenzene, ethylene glycol di(meth)acrylate, and combinations thereof. In some embodiments, the crosslinker may comprise linked divinylbenzene, such as a plurality of divinylbenzene compounds linked by variable linker compositions and lengths. Other exemplary crosslinkers include styrenic and methacrylic based compounds. While not wishing to be bound by theory, it is believed that the type and structure of the crosslinker may have an effect on the ability of the polymer bead to expand substantially uniformly in different reagents, such as in polar and non-polar solvents.

The crosslinker may comprise trimethylolpropane triacrylate, hexanediol diacrylate, tetraethylene glycol dimethacrylate, bisphenol A diglycidyl ether, hexamethylene diisocyanate, pentaerythritol triacrylate, diallyl maleate, poly(propylene glycol) dimethacrylate, bisphenol A glycerolate dimethacrylate, 1,6-hexanediol diacrylate, methacrylic anhydride, pentaerythritol tetraacrylate, allyl methacrylate, 1,3,5-Triallyl-1,3,5-triazine-2,4,6(1H,3H,5H)-trione, dipentaerythritol hexaacrylate, tricyclodecane dimethanol diacrylate, or a combination thereof.

Nucleotides are the basic building blocks of an oligonucleotide (strands of RNA or DNA). Nucleotides typically include a five carbon sugar molecule (either ribose for RNA or deoxyribose for DNA) attached to a phosphate group and a nitrogen-containing base, also referred to as a nucleobase herein. Nucleobases include adenine (A), guanine (G), cytosine (C), and thymine (T) (DNA) or adenine (A), guanine (G), cytosine (C), and uracil (U) (RNA). A nucleoside refers to the sugar molecule and nucleobase of the nucleotide, without the phosphate group. During oligonucleotide synthesis, a first nucleoside is bound to the solid support by the 3' hydroxyl of the sugar molecule. Additional nucleosides are typically sequentially linked in the 3' to 5' direction to form the oligonucleotide.

Thus, the copolymer beads may be capable of binding a nucleoside, nucleoside analog, or derivative thereof. For instance, the functionalized repeating motif may be capable of binding a nucleoside, nucleoside analog, or derivative thereof. The nucleoside, nucleoside analog, or derivative thereof may be covalently bound to a terminal hydroxyl or amine functional group of the bead.

During oligonucleotide synthesis, typically the nucleobase may include a protecting group (a nucleobase having a protecting group is also referred to as a protected nucleobase herein) attached to the exocyclic amine. For instance, A, G, and C nucleobases have an exocyclic amine that may require a protecting group during synthesis. Typically protecting groups include a benzoyl group (A), an isobutyryl group (G), and an acetyl group (C). However, other protecting groups may be used.

One exemplary repeating motif having a bound nucleoside derivative is represented by the compound of formula (IV):

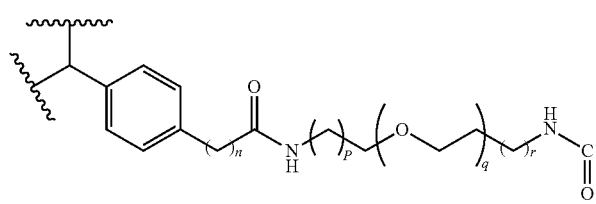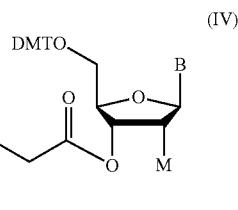

(IV)

wherein n is 0 or 1; p is 1-6; q is 0-3; r is 1-6; B is a nucleobase, a protected nucleobase, a nucleobase analog, or a protected nucleobase analog; M is H, a protected hydroxyl, O-alkyl, 2-methoxyethanolate (MOE), F, or a methylene linked to C4' of the ribose.

In some embodiments, the nucleoside, nucleoside analog, or derivative thereof may be bound to the functionalized repeating motif by a cleavable linker. One exemplary compound having a nucleoside derivative bound by a cleavable linker is represented by the compound of formula (IV-A):

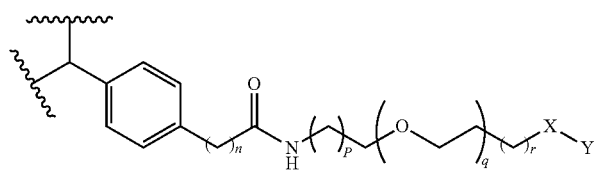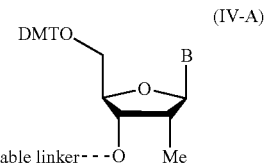

(IV-A)

wherein n is 0 or 1; p is 1-6; q is 0-3; r is 1-6; B is a nucleobase, a protected nucleobase, a nucleobase analog, or a protected nucleobase analog; M is H, a protected hydroxyl, O-alkyl, 2-methoxyethanolate (MOE), F, or a methylene linked to C4' of the ribose; X is O or NH, when X is O, Y is C=O, PO$_2$, or NC—(CH$_2$—CH$_2$)—O—P(=O); when X is NH, Y is C=O.

In accordance with one aspect, there is provided a resin of copolymer beads. As disclosed herein, a resin generally refers to a plurality of copolymer beads. The resin may be provided in dried form or in solvated form.

While not wishing to be bound by theory, it is believed that certain properties of the copolymer bead enable the beads to achieve more uniform expansion in different reagents, such as in polar and non-polar reagents. Such properties include, for example, one or more of average bead diameter, swelling volume, pore size, pore volume, porosity, surface area, amount of crosslinker, and amount of functionalized repeating motif. Furthermore, it is believed that the type of crosslinker used may have an effect on expansion properties of the copolymer bead.

In certain embodiments, the copolymer bead may have a diameter between 10 μm and 300 μm, as measured according to the Coulter principle. The copolymer bead may have a diameter between 30 μm and 200 μm, between 40 μm and 150 μm, or between 50 μm and 90 μm. The Coulter principle, also known as the electrical sensing zone, is a particle measurement method known to those of skill in the art that generally involves suspending the particles in a conductive liquid to pass through a narrow orifice, through which the particles are counted while voltage change is measured. The voltage change as particles pass through the orifice is proportional to particle volume. Thus, particle dimensions are quantified based on measured voltage change.

A resin may be characterized as comprising copolymer beads having an average bead diameter between 10 μm and 300 μm, between 30 μm and 200 μm, between 40 μm and 150 μm, or between 50 μm and 90 μm. In certain embodiments, the resin has an average diameter of about 50-60 μm, for example, about 55 μm. In certain embodiments, the resin has an average diameter of about 80-90 μm, for example, about 85 μm. In certain embodiments, the resin has an average diameter of about 90-110 μm, for example, about 100 μm.

The copolymer beads may be substantially spherical. For instance, the beads may appear spherical to the eye when viewed at a magnification sufficient to view the shape of individual particles.

The copolymer beads may be provided in a dry state or in a solvated state, for example, partially solvated or solvent wetted state or as a slurry in solvent. When solvated, the copolymer beads may expand or swell to a predetermined volume. In certain embodiments, the expanded volume is less than 5 times the dry volume, for example less than 3 times the dry volume. The expanded volume may be between 1 and 4 times the dry volume, for example, between 2 and 3 times the dry volume. A greater swelling volume may reduce the amount of dry resin needed to load a column for synthesis. However, a greater swelling volume may also contribute to a greater difference in bead expansion across different reagents. Thus, a lesser swelling volume may provide more uniform expansion.

The copolymer beads may have a porous structure when expanded. In some embodiments, when expanded, the copolymer bead may have a porosity of at least about 10%, for example, the copolymer bead may have a porosity of between 10% and 25%, between 25% and 50%, between 50% and 75%, or more than 75%.

In some embodiments, the copolymer may be at least 10% crosslinked, for example, the copolymer may be 10-20% crosslinked, 20-30% crosslinked, 30-40% crosslinked, 40-50% crosslinked, 50-60% crosslinked, 60-70% crosslinked, 70-75% crosslinked, 75-80% crosslinked, 80-85% crosslinked, 85-90% crosslinked, 90-95% crosslinked, or more than 95% crosslinked.

Additionally, it is believed that a narrower particle size distribution of the copolymer beads in a resin may produce a more consistent product. In some embodiments, the resin may be substantially monodispersed. As used herein, a monodispersed resin may have a particle size distribution with a span (D90–D10)/(D50) 0.8 or less, for example, 0.8-0.7, 0.7 or less, 0.7-0.6, 0.6 or less, 0.6-0.5, or 0.5 or less, where D90 is the diameter at which 90% of the total particles have a smaller diameter, D10 is the diameter at which 10% of the total particles have a smaller diameter, and D50 is the diameter at which 50% of the total particles have a smaller diameter. In other embodiments, the resin may be more polydisperse. A polydisperse resin may have a particle size distribution with a span (D90–D10)/(D50) greater than 0.5, greater than 0.6, greater than 0.7, or greater than 0.8.

The copolymer beads disclosed herein may be produced by several methods. One exemplary method is suspension polymerization, which involves the combination and stirring of a continuous phase and a dispersed phase to produce an emulsion. During suspension polymerization, typically a dispersed phase including the monomers, crosslinking agent, an initiator, and a diluent is stirred in a continuous phase including a solvent to produce the emulsion. The monomer and initiator are typically immiscible and sparingly soluble in the aqueous continuous phase. Monomer droplets may be formed inside the aqueous medium and suspended with stirring. Polymerization may be initiated on the droplets which lead to polymer chain growth. As chain length increases, the monomers that have formed polymer chains are no longer soluble and start to convert to a solid form. While not wishing to be bound by theory, it is believed that droplet properties may be controlled by stirrer speed, shear forces, geometry of the stirrer, and geometry of the reactor.

Droplet formation may be achieved in a number of ways, including simple stirring (most commonly used technique) or seeded swelling processes, either with polymeric or monomeric seed particles or droplets. Additionally, the method of droplet formation may have an effect on the size distribution of the produced beads. Thus, a substantially monodisperse resin may be produced by controlling droplet formation. However, an optional size classification step may be performed after production of the copolymer beads to obtain a resin having a more monodisperse size distribution.

In accordance with one aspect, there is provided an emulsion comprising a continuous phase and a dispersed phase. The emulsion is an intermediate product in the production of the copolymer beads disclosed herein. The continuous phase may comprise a solvent. The solvent may be any solution in which the dispersed phase is immiscible. The solvent may be an aqueous solution. In certain embodiments, the solvent is an aqueous solution including a surfactant and/or a stabilizer. Exemplary surfactants include polyvinyl alcohol (PVA) and sodium dodecyl sulfate (SDS). An initiator may be used to initiate the polymerization reaction. One exemplary initiator is azobisisobutyronitrile (AIBN).

The dispersed phase may comprise the monomers and crosslinking agent and an effective amount of the diluent to produce the copolymer bead. The monomers may include a first monomer and a second monomer, which will polymerize to form the first repeating motif and the second repeating motif, respectively. The first monomer may be a styrene monomer. The second monomer may be a functional monomer comprising a substituted styrene having an ester functional group or an amide with a terminal hydroxyl or amine functional group.

In certain embodiments, the second monomer in the dispersed phase is a substituted styrene having an ester functional group of formula (I-A):

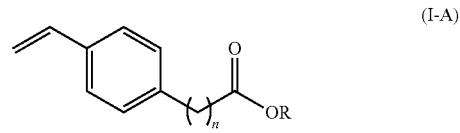

wherein n is an integer between 0 and 12, and R is a $C_1$-$C_6$ alkyl, a substituted alkyl, a phenyl or a substituted phenyl.

In other embodiments, the second monomer in the dispersed phase is a substituted styrene having an amide with a terminal hydroxyl or amine functional group similar to the compound of formula (I-A), but in which the O—R is substituted with NH—$R^2$-Q, wherein $R^2$ is a $C_1$-$C_{36}$ alkyl or a $C_1$-$C_{36}$ substituted alkyl, and Q is $NH_2$ or OH.

The dispersed phase may also comprise a diluent. Exemplary diluents include toluene, isopropyl alcohol, diethylbenzene, ethyl acetate, cyclohexanone, and combinations thereof. Other exemplary diluents include 1-octanol, benzaldehyde, benzyl alcohol, benzyl benzoate, butyl benzoate, butyl stearate, dibutyl sebacate, Di(2-ethylhexyl) phthalate, diethyl malonate, diethylene glycol, diethylene glycol butyl ether, diethylene glycol butyl ether acetate, dimethyl phthalate, dioctyl phthalate, dioctyl adipate, di-n-octyl phthalate, dioctyl sebacate, diphenyl ether, diphenyl ketone, Dodecanol, Dodecylamine, dotriacontane, ethyl acetoacetate, ethyl benzoate, ethylene glycol, glycerol, glyceryl triacetate, hexadecanoic acid, hexadecanol, hexadecylamine, methyl benzoate, methyl salicylate, methyl stearate, myristic acid, octanoic acid, oleic acid, propylene glycol, stearic acid, stearyl alcohol, tetradecylamine, tetramethylene sulfone, tributyl citrate, tributyl phosphate, triethyl citrate, triethyl phosphate, triethylene glycol, trimethyl phosphate, trioctyl phosphate, acetophenone, acetyl tributyl citrate, acetyl triethyl citrate, cyclohexanone, decalin, dibutyl maleate, dibutyl phthalate, diethyl phthalate, diethylene glycol monoethyl ether acetate, diisodecyl phthalate, dimethyl sulfoxide, diphenyl methane, eicosane, hexamethyl benzene, propylene carbonate, tetradecane, γ-butyrolactone, ε-caprolactam, and combinations thereof.

While not wishing to be bound by theory, it is believed that the type and/or amount of the diluent in the emulsion may be selected to control properties of the polymerized bead, such as swelling volume, pore size, pore volume, pore morphology, and/or porosity. In some embodiments, the effective amount of the diluent is selected to produce a copolymer bead having target properties. For example, the effective amount of the diluent may be selected to produce a copolymer bead having a target porosity and surface area when expanded.

In some embodiments, the emulsion components that produce the copolymer bead may comprise between 45 vol % and 85 vol % of the diluent. The effective amount of the diluent may be from 60 vol % to 75 vol %, for example, 60 vol % to 65 vol %, 65 vol % to 70 vol %, or 70 vol % to 75 vol %. In certain exemplary embodiments, the effective amount of the diluent may be about 70 vol %, about 71 vol %, about 72 vol %, about 73 vol %, about 74 vol %, or about 75 vol %. In practice, the effective amount of the diluent may be +/−5 vol % of the disclosed ranges.

The emulsion components that produce the polymer bead may comprise between 7 vol % to 16 vol % of the crosslinking agent. For instance, the emulsion components that produce the polymer bead may comprise from about 7 vol % to about 10 vol %, from about 10 vol % to about 12 vol %, or from about 12 vol % to about 16 vol % of the crosslinking agent. In practice, the emulsion components that produce the polymer bead may comprise +/−1 vol % of the disclosed ranges. In some embodiments, the crosslinking agent may have a purity of at least 30%, for example, at least 40%, at least 50%, at least 60%, at least 70%, at least 80%, at least 90%, or at least 95%.

The emulsion components that produce the polymer bead may comprise between 2 vol % and 30 vol % of each of the first and second monomer, independently. For instance, the emulsion components that produce the polymer bead may comprise between 2 vol % and 5 vol %, between 5 vol % and 10 vol %, between 10 vol % and 15 vol %, between 15 vol % and 20 vol %, between 20 vol % and 25 vol %, or between 25 vol % and 30 vol % of each of the first and second monomer.

The emulsion components that produce the polymer bead may comprise a greater amount of the first monomer than of the second (functionalized) monomer. In certain embodiments, an amount of the first monomer is about 1 to 10 times (1×-4×) an amount of the second monomer. For instance, an amount of the first monomer may be about equivalent to an amount of the second monomer (1×), or an amount of the first monomer may be about 2×, 3×, 4×, 5×, 6×, 7×, 8×, 9×, or 10× an amount of the second monomer.

In some embodiments, for example, when a functionalized monomer having an ester group is used in the copolymer bead polymerization process, the production method may include converting the ester functional group into an amide having a terminal hydroxyl or amine functional group, as previously described. In one exemplary method of conversion, the copolymer beads having the ester group functionalized repeating motif may be suspended in a reagent, such as diamine or an amine alcohol (e.g., hydroxy alkyl amine) and heated. One exemplary amine alcohol is ethanolamine. The copolymer beads may then be isolated and vacuum dried to reveal copolymer beads having an amide with a terminal hydroxyl or amine functional group.

In other embodiments, a functionalized monomer having an ester group may be converted into an amide having a terminal hydroxyl or amine functional group prior to polymerization of the monomer into the copolymer bead.

In accordance with another aspect, there is provided a method of synthesizing a target oligonucleotide. Synthesis may be initiated by covalently binding a nucleoside, nucleoside analog, or derivative thereof to the bead. As previously described, the 3' hydroxyl of the sugar molecule may be covalently attached to a terminal hydroxyl or amine functional group of the repeating motif. In other embodiments, the 3' hydroxyl of the sugar molecule may be covalently bound to a cleavable linker which is bound to the terminal hydroxyl or amine functional group of the repeating motif.

In accordance with yet another aspect, there is described a method of facilitating oligonucleotide synthesis. The method may include providing a resin formed of copolymer beads as disclosed herein. The method may also include providing instructions to combine the resin with an effective amount of a solution comprising nucleosides, nucleoside analogs, or derivatives thereof to couple at least one nucleoside or nucleoside analog to a plurality of the copolymer beads. Optionally, the nucleosides, nucleoside analogs, or derivates thereof may be protected, i.e., including a protecting group. In certain embodiments, the effective amount of the solution comprising nucleosides, nucleoside analogs, or derivatives thereof is from about 200 to about 600 µmol of nucleoside, nucleoside analog, or nucleoside derivative per gram of the resin.

In certain embodiments, the resin may be provided in dry powder form. The method may comprise providing instructions to load the dry form resin in a column, for example, in a fixed bed column. In other embodiments, the resin may be provided in a solvated or expanded form. Optionally, the resin may be provided in a column, such as the fixed bed column.

EXAMPLES

The function and advantages of these and other embodiments can be better understood from the following examples. These examples are intended to be illustrative in nature and are not considered to be limiting the scope of the disclosure.

Example 1: Production of Copolymer Beads by Suspension Polymerization

Copolymer beads may be produced by the exemplary method summarized in the schematic diagram of FIG. 1. Monomers of a crosslinking monomer (divinyl benzene (DVB)), monomers of styrene, and monomers of styrene including a functional group (Styrene-FG) (here, ester groups), are combined under stirred suspension polymerization or seed polymerization with a diluent (toluene) and an initiator (azobisisobutyronitrile (AIBN)) in a solvent (polyvinyl alcohol/sodium dodecyl sulfate (PVA/SDS) in water). Polymerization is initiated by increasing the temperature to 65° C.

The polymerization reaction produces a population of solid phase macroreticular particles having a size of 50 to 100 µm, and having multiple voids that form a porous structure, in particular, in the solvated state. After polymerization, an ester functional group (FG) can be converted to an amide having a terminal amino/hydroxyl functional group, as described in Examples 4-5. A cleavable linker and/or a nucleoside can be attached to the copolymer bead, as described in Example 6.

Copolymer beads were produced by the method described above. The composition of the dispersed phase (not including initiator) for each sample is shown in Table 1.

TABLE 1

| | Chemical Composition of Diverse Copolymer Beads | | | | | |
|---|---|---|---|---|---|---|
| Descriptor | Styrenic monomers* Styrene and ethyl vinyl benzene (vol %) | Functional group monomer Substituted styrene (vol %) | Crosslinker DVB (vol %) | Diluent Toluene (vol %) | Seed | Functional group monomer |
| Copolymer bead | 15.5 | 2.1 | 7.6 | 73.4 | 1.5 | 1-chloromethyl-4-vinyl benzene |

TABLE 1-continued

Chemical Composition of Diverse Copolymer Beads

| Descriptor | Styrenic monomers* Styrene and ethyl vinyl benzene (vol %) | Functional group monomer Substituted styrene (vol %) | Crosslinker DVB (vol %) | Diluent Toluene (vol %) | Seed | Functional group monomer |
|---|---|---|---|---|---|---|
| Proto X3 | 9.2 | 3.8 | 11.6 | 75.4 | 0.0 | Methyl 2-(4-vinylphenyl)acetate |
| Proto_1 | 19.1 | 3.2 | 7.5 | 68.9 | 1.3 | 1-chloromethyl-4-vinyl benzene |
| Proto_2 | 27.3 | 3.7 | 3.8 | 63.6 | 1.6 | 1-chloromethyl-4-vinyl benzene |
| Proto_3 | 10.1 | 2.6 | 11.6 | 74.6 | 1.1 | 1-chloromethyl-4-vinyl benzene |
| Proto_4 | 19.6 | 3.7 | 11.7 | 63.4 | 1.6 | 1-chloromethyl-4-vinyl benzene |
| Proto_5 | 18.2 | 2.4 | 3.7 | 74.6 | 1.1 | 1-chloromethyl-4-vinyl benzene |
| Proto_8 | 9.6 | 3.2 | 11.6 | 74.5 | 1.1 | 1-chloromethyl-4-vinyl benzene |
| Proto_9 | 18.5 | 4.6 | 11.8 | 63.5 | 1.6 | 1-chloromethyl-4-vinyl benzene |
| Proto_13 | 9.1 | 3.8 | 11.6 | 74.4 | 1.1 | Methyl 2-(4-vinylphenyl)acetate |
| Proto_13 XL | 7.7 | 4.8 | 11.2 | 75.2 | 1.1 | Methyl 2-(4-vinylphenyl)acetate |
| Proto_13 XXL | 6.7 | 5.7 | 11.3 | 75.2 | 1.1 | Methyl 2-(4-vinylphenyl)acetate |
| Proto_13XXL-D76_C10 | 6.1 | 4.7 | 9.4 | 78.9 | 0.9 | Methyl 2-(4-vinylphenyl)acetate |
| Proto_13-D72_C8 | 13.0 | 3.8 | 7.4 | 74.7 | 1.1 | Methyl 2-(4-vinylphenyl)acetate |
| Proto_13-D72_C10 | 11.1 | 3.8 | 9.4 | 74.6 | 1.1 | Methyl 2-(4-vinylphenyl)acetate |
| Proto_13-D72_C14 | 7.7 | 3.8 | 12.9 | 74.5 | 1.1 | Methyl 2-(4-vinylphenyl)acetate |
| Proto_13-D76_C12 | 6.6 | 3.2 | 11.0 | 78.3 | 0.9 | Methyl 2-(4-vinylphenyl)acetate |
| Proto_13-D78_C12 | 4.8 | 2.9 | 10.8 | 80.6 | 0.9 | Methyl 2-(4-vinylphenyl)acetate |
| Proto 13B | 9.7 | 3.5 | 11.0 | 74.7 | 1.1 | Methyl 4-vinylbenzoate |
| Proto_14 | 18.4 | 5.5 | 11.6 | 62.9 | 1.6 | Methyl 2-(4-vinylphenyl)acetate |
| Proto_14 XL | 14.9 | 8.2 | 11.5 | 63.8 | 1.6 | Methyl 2-(4-vinylphenyl)acetate |
| Proto_14 XXL | 10.4 | 11.6 | 11.6 | 64.8 | 1.6 | Methyl 2-(4-vinylphenyl)acetate |
| Proto_23 | 9.1 | 3.9 | 11.5 | 75.2 | 0.3 | Methyl 2-(4-vinylphenyl)acetate |
| Proto_23 XXL | 6.9 | 5.8 | 11.6 | 75.4 | 0.3 | Methyl 2-(4-vinylphenyl)acetate |
| Proto_23 XXL_D76_C10 | 6.2 | 5.0 | 9.5 | 79.0 | 0.3 | Methyl 2-(4-vinylphenyl)acetate |

Example 2: Swelling

Swell tests were carried out by weighing 1 g of produced copolymer beads into a 10 mL measuring cylinder. Solvent was then added to make up the total volume to the 10 mL mark. The particles were sonicated in solvent for 10 minutes and allowed to expand overnight. While particles are typically expanded within 10 minutes, the samples were allowed to expand overnight to ensure full expansion was achieved.

Figure 2A:
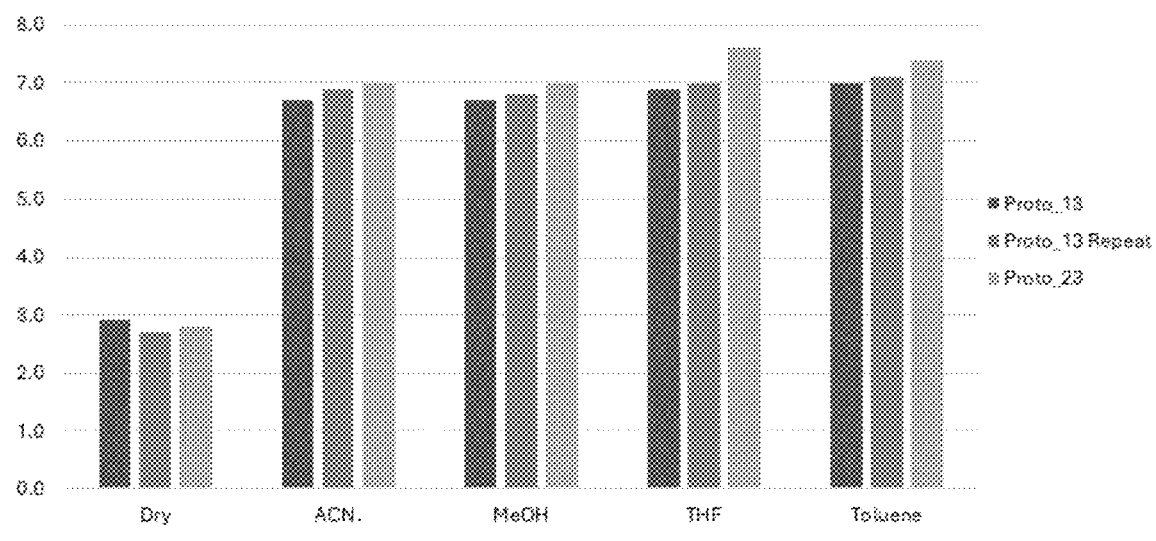
FIGS. 2A-2B are graphs showing particle expansion in polar and non-polar solvents.
Figure 2B:
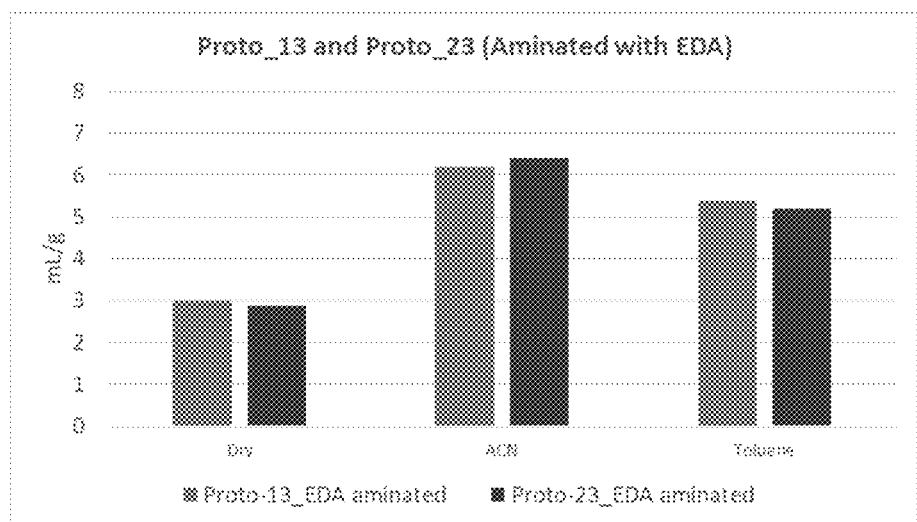

Expansion of the tested particles is shown in the graphs of FIGS. 2A-2B. In particular, the graph of FIG. 2A is a comparison of particle swelling in polar and non-polar solvents, pre-surface functionalization; FIG. 2B is a comparison of particle swelling in polar and non-polar solvents, post-amination with ethylenediamine (EDA).

Example 3: Size Distribution

Figure 3:
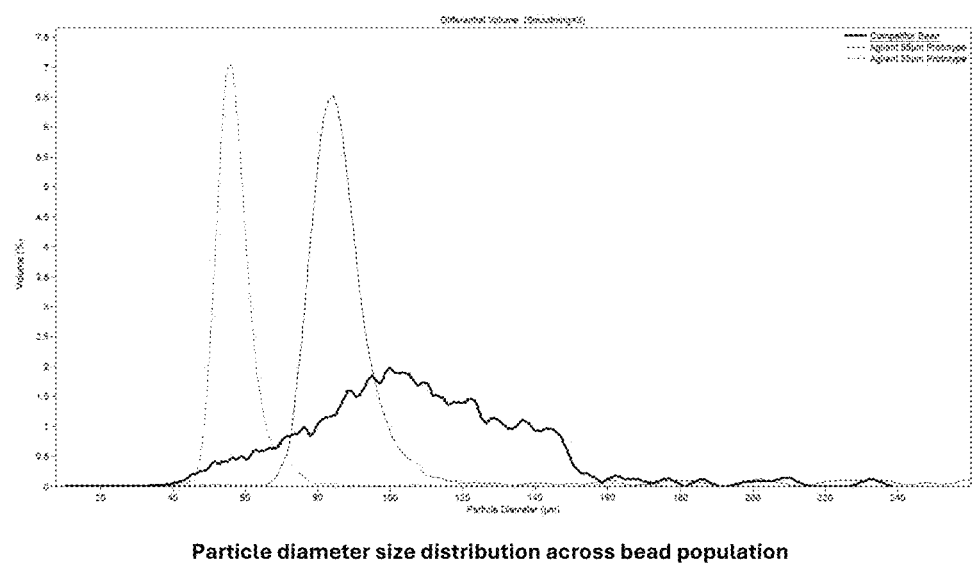
FIG. 3 is a graph showing particle diameter size distribution across bead population.
Figure 4:
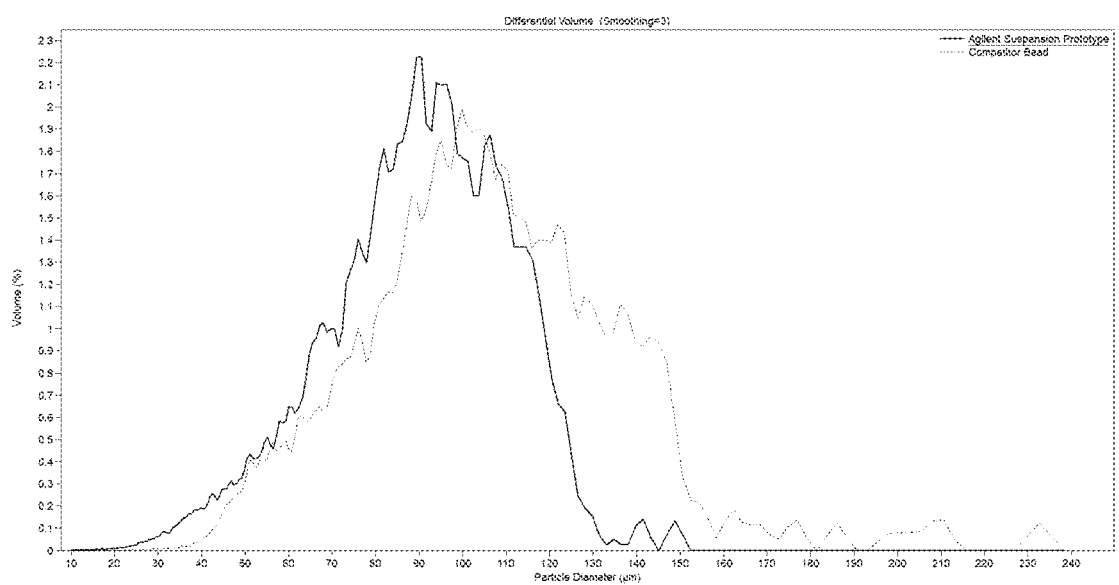
FIG. 4 is a graph showing particle diameter size distribution across a population of beads made by suspension polymerization.

Size distribution of the produced copolymer beads was measured. To determine particle size, 50 mg of polymeric particles were dispersed in a solution of 2% SDS wt:wt in water. The particles were then added by pipette to a stirred solution of ISOTON II diluent (Beckman Coulter). The particle size was measured according to the Coulter Principle using a 400 µm aperture. Particle volume was measured with a Multisizer™ 3 instrument (Beckmann Coulter). Size distribution is shown in the graphs of FIGS. 3-4.

Example 4: Conversion of Ester Group on Copolymer Beads to Amide Group Using Diamines I. Conversion of Methyl 2-(4-Polymer Linked) Phenylacetate to Reactive Amide/Amines Using Neat Diamines Methyl 2-(4-vinylphenyl)acetate monomers were co-polymerized with styrene and divinylbenzene to produce polystyrene beads having a substituted styrene of formula (I) (n=1, $R^1$=$CH_3$). One gram of the copolymer beads was suspended in 10 mL (8.99 g, 150 mmol) neat, anhydrous, 1,2-ethylene diamine (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine. The suspended beads were heated and shaken for 12 hours at 100° C. After 12 hours the heater was turned off and the flask was allowed to cool to room temperature. The beads were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads of formula (II) functionalized with terminal amine groups (1,2-ethylene diamine, Q=$NH_2$, p=2) were then placed under high vacuum 170 mbar for 2 hr. to remove all residual solvent and the amine loading determined.

Copolymer beads having an ester functional group were successfully converted to beads having an amide functional group.

II. Conversion of Methyl 2-(4-Polymer Linked) Phenylacetate to Reactive Amide/Amines Using Diamines Dissolved in Toluene Methyl 2-(4-vinylphenyl)acetate monomers were co-polymerized with styrene and divinylbenzene to produce polystyrene beads having a substituted styrene of formula (I) (n=1, $R^1$=$CH_3$). One gram of the produced beads was suspended in 10 mL of a 50% w/v solution, of anhydrous, 1,2-ethylene diamine (4.5 g, 75 mmol) dissolved in anhydrous toluene (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine solution. The suspended beads were heated and shaken for 12 hours at 100° C. After 12 hours the heater was turned off and the flask allowed to cool to room temperature. The beads were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads of formula (II) functionalized with terminal amine groups (1,2-ethylene diamine, Q=$NH_2$, p=2) were then placed under high vacuum 170 mbar for 2 hr. to remove all residual solvent and the determine amine loading.

Copolymer beads having an ester functional group were successfully converted to beads having an amide with a terminal amine functional group.

III. Conversion of Methyl 2-(4-Polymer Linked) Phenylacetate to Reactive Amide/Amines Using Neat (Polyethylene Glycol) Peg-Diamines Methyl 2-(4-vinylphenyl)acetate monomers were co-polymerized with styrene and divinylbenzene to produce polystyrene beads having a substituted styrene of formula (I) (n=1, $R^1$=$CH_3$). One gram of the produced beads was suspended in 10 mL (9.61 g, 150 mmol) neat, anhydrous, 2,2'-oxydiethanamine (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine. The suspended beads were heated and shaken for 12 hours at 100° C. After 12 hours the heater was turned off and the flask allowed to cool to room temperature. The beads of formula (III) functionalized with terminal amine groups (Q=$NH_2$, p=1, q=1, r=0) were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads were then placed under high vacuum 170 mbar for 2 hr to remove all residual solvent and the amine loading determined.

Figure 6:
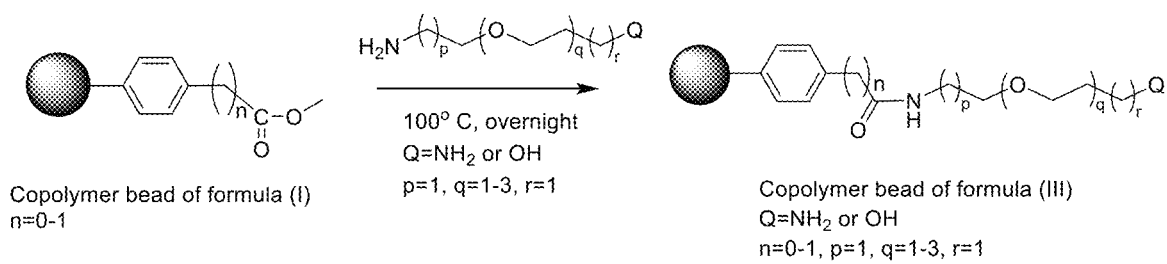
FIG. 6 is a schematic diagram showing the conversion of ester groups (beads of formula (I)) to amine or hydroxyl groups (beads of formula (III)), according to one embodiment.

The same procedure was repeated respectively with pegamines having respectively 2 or 3 peg units, wherein n=1, Q=$NH_2$, p=1, q=2-3, r=0 (FIG. 6).

In each instance, copolymer beads having an ester functional group were successfully converted to beads having an amide functional group.

IV. Conversion of Methyl 2-(4-Polymer Linked) Benzoate to Reactive Amide/Amines Using Neat Diamines Methyl 4-vinylbenzoate monomers were co-polymerized with styrene and divinylbenzene to produce polystyrene beads having a substituted styrene of formula (I) (n=0, $R^1$=$CH_3$). One gram of the produced beads was suspended in 10 mL (8.99 gr, 150 mmol) neat, anhydrous, 1,2-ethylene diamine (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine. The suspended beads were heated and shaken for 12 hours at 100° C. After 12 hours the heater was turned off and the flask allowed to cool to room temperature. The beads of formula (II) functionalized with amine groups (n=0, Q=$NH_2$ and p=2) were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads were then placed under high vacuum 170 mbar for 2 hr. to remove all residual solvent and the amine loading determined.

Figure 5:
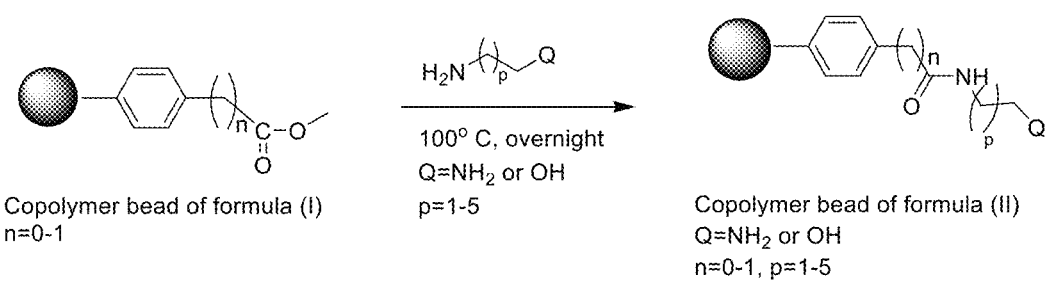
FIG. 5 is a schematic diagram showing the conversion of ester groups (beads of formula (I)) to amine or hydroxyl groups (beads of formula (II)); according to one embodiment.

The same procedure was repeated with 1,3-propane diamine (known as trimethylene diamine), 1,4-butane diamine, 1,5-pentane diamine, or 1,6-hexane diamine to produce beads of formula (II), functionalized with terminal amines and linkers of different lengths wherein n=0, Q=$NH_2$ and p varies from 3 to 6 (FIG. 5).

In each instance, copolymer beads having an ester functional group were successfully converted to beads having an amide functional group.

V. Conversion of Methyl 2-(4-Polymer Linked) Benzoate to Reactive Amide/Amines Using Diamines Dissolved in Toluene Methyl 4-vinylbenzoate monomers were co-polymerized with styrene and divinylbenzene to produce polystyrene beads having a substituted styrene of formula (I) (n=0, $R^1$=$CH_3$). One gram of the produced beads were suspended in 10 mL of a 50% w/v solution, of anhydrous, 1,2-ethylene diamine (4.5 gr, 75 mmol) dissolved in anhydrous toluene (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine solution. The suspended beads were heated and shaken for 12 hours at 100° C. After 12 hours the heater was turned off and the flask allowed to cool to room temperature. The beads of formula (II) functionalized with amine groups (n=0, Q=$NH_2$ and p=2) were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads were then placed under high vacuum 170 mbar for 2 hr. to remove all residual solvent and the amine loading determined.

Copolymer beads having an ester functional group were successfully converted to beads having an amide functional group.

VI. Conversion of Methyl 2-(4-Polymer Linked) Benzoate to Reactive Amide/Amines Using Neat Peg-Diamines Methyl 4-vinylbenzoate monomers were co-polymerized with styrene and divinylbenzene to produce copolymer beads having a substituted styrene of formula (I) (n=0, $R^1$=$CH_3$). One gram of the produced beads were suspended in 10 mL (9.61 gr, 150 mmol) neat, anhydrous, 2,2'-oxydiethanamine (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine. The suspended beads were heated and shaken for 12 hours at 100° C. After 12 hours the heater was turned off and the flask allowed to cool to room temperature. The beads of formula (III) functionalized with terminal amine groups (n=0, Q=$NH_2$, p=1, q=1, r=0) were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads were then placed under high vacuum 170 mbar for 2 hr to remove all residual solvent and the amine loading determined.

The same procedure was repeated respectively with peg-diamines having 2 or 3 peg units, wherein n=0, Q=$NH_2$, p=1, q=2-3, r=0 (FIG. 6).

In each instance, copolymer beads having an ester functional group were successfully converted to beads having an amide with a terminal amine functional group.

Example 5: Conversion of Ester Group on Copolymer Beads to Amide Group Using Hydroxy Alkyl Amine I. Conversion of Methyl 2-(4-Polymer Linked) Phenylacetate to Reactive Amide/Hydroxyls Using Neat Hydroxy Alkyl Amine Methyl 2-(4-vinylphenyl)acetate monomers were co-polymerized with styrene and divinylbenzene into the polystyrene bead having substituted styrene of formula (I) (n=1, $R^1$=$CH_3$). One gram of the produced beads was suspended in 10 mL (8.99 g, 150 mmol) neat, anhydrous, ethanolamine (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine. The suspended beads were heated and shaken for 12 hours at 100° C. After 12 hours the heater was turned off and the flask allowed to cool to room temperature. The beads were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads of formula (II) functionalized with hydroxyl groups (Q=OH, p=2) were then placed under high vacuum 170 mbar for 2 hr to remove all residual solvent.

Figure 8:
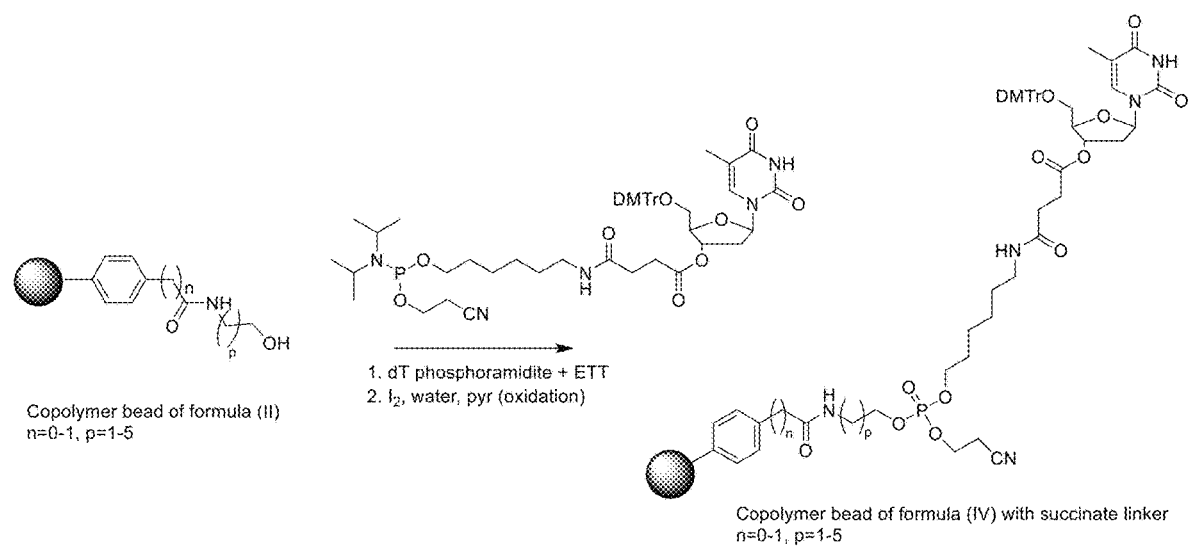
FIG. 8 is a schematic diagram showing loading of a bead of formula (II) with nucleoside through a succinate linker dT amidite, according to one embodiment.

The hydroxyl groups were used to attach a protected nucleoside by reacting 50 mg of copolymer resin with 94 mg, 0.1 mmol of Thymidine, 5'-O-[bis(4-methoxyphenyl) phenylmethyl]-3'-[13-(2-cyanoethoxy)-15-methyl-14-(1-methylethyl)-4-oxo-12-oxa-5,14-diaza-13-phosphahexadecanoate] (ChemeGenes), dissolved in anhydrous acetonitrile at 0.1M in the presence of 0.1 M 5-(Ethylthio)-1H-tetrazole (Sigma-Aldrich) for 10 minutes at room temperature (as depicted in FIG. 8, wherein ETT is 5-Ethylthio-1H-Tetrazole). The hydroxyl loading was determined using an absorbance assay for the dimethoxytrityl protective group that was cleaved in acidic solution from the 5'-hydroxyl of the nucleoside attached to the support.

The same procedure was repeated respectively with 3-amino-1-propanol, 4-amino-1-butanol, 5-amino-1-pentanol, or 6-amino-1-hexanol to produce beads of formula (II), functionalized with terminal hydroxyls and linkers of different lengths, wherein n=1, Q=OH and p varies from 3 to 6, as shown in FIG. 5.

In each instance, copolymer beads having an ester functional group were successfully converted to beads having an amide with a terminal hydroxyl functional group.

II. Conversion of Methyl 2-(4-Polymer Linked) Phenylacetate to Reactive Amide/Alcohols Using Neat Peg-Hydroxy Alkyl Amine Methyl 2-(4-vinylphenyl)acetate monomers were co-polymerized with styrene and divinylbenzene to produce polystyrene beads having a substituted styrene of formula (I) (n=1, $R^1$=$CH_3$). One gram of the produced beads was suspended in 10 mL (10.6 g, 100 mmol) neat, anhydrous, 2-(2-aminoethoxy) ethanol (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine. The suspended beads were heated and shaken for 12 hours at 100° C. After 12 hours the heater was turned off and the flask allowed to cool to room temperature. The beads of formula (III) functionalized with hydroxyl groups (Q=OH, p=1, q=1, r=0) were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads were then placed under high vacuum 170 mbar for 2 hr to remove all residual solvent.

The hydroxyl groups were used to attach a protected nucleoside by reacting 50 mg of copolymer resin with 94 mg, 0.1 mmol of Thymidine, 5'-O-[bis(4-methoxyphenyl) phenylmethyl]-3'-[13-(2-cyanoethoxy)-15-methyl-14-(1-methylethyl)-4-oxo-12-oxa-5,14-diaza-13-phosphahexadecanoate] (ChemeGenes), dissolved in anhydrous acetonitrile at 0.1M in the presence of 0.1 M 5-(Ethylthio)-1H-tetrazole (Sigma-Aldrich) for 10 minutes at room temperature. The hydroxyl loading was determined using an absorbance assay for the dimethoxytrityl protective group that was cleaved in acidic solution from the 5'-hydroxyl of the nucleoside attached to the support.

Copolymer beads having an ester functional group were successfully converted to beads having an amide with a terminal hydroxyl functional group, that was subsequently used to attach a nucleoside derivative.

III. Conversion of Methyl 2-(4-Polymer Linked) Benzoate to Reactive Amide/Hydroxyls Using Neat Hydroxy Alkyl Amine Methyl 4-vinylbenzoate monomers were co-polymerized with styrene and divinylbenzene to produce polystyrene beads having a substituted styrene of formula (I) (n=0, $R^1$=$CH_3$). One gram of the produced beads was suspended in 10 mL (8.99 gr, 150 mmol) neat, anhydrous, ethanolamine (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine. The suspended beads were heated and shaken for 12 hours at 100° C. After 12 hours the heater was turned off and the flask allowed to cool to room temperature. The beads of formula (II) functionalized with hydroxyl groups (n=0, Q=OH and p=2) were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads of formula (II) were then placed under high vacuum 170 mbar for 2 hr to remove all residual solvent.

The hydroxyl groups were used to attach a protected nucleoside by reacting 50 mg of copolymer resin with 94 mg, 0.1 mmol of Thymidine, 5'-O-[bis(4-methoxyphenyl) phenylmethyl]-3'-[13-(2-cyanoethoxy)-15-methyl-14-(1-methylethyl)-4-oxo-12-oxa-5,14-diaza-13-phosphahexadecanoate] (ChemeGenes), dissolved in anhydrous acetonitrile at 0.1M in the presence of 0.1 M 5-(Ethylthio)-1H-tetrazole (Sigma-Aldrich) for 10 minutes at room temperature. The hydroxyl loading was determined using an absorbance assay for the dimethoxytrityl protective group born of the 5'-hydroxyl of the thymidine nucleoside (FIG. 8).

Copolymer beads having an ester functional group were successfully converted to beads having an amide with a terminal hydroxyl functional group that was then subsequently used to attach a nucleoside derivative.

IV. Conversion of Methyl 2-(4-Polymer Linked) Benzoate to Reactive Amide/Alcohols Using Neat Peg-Hydroxy Alkyl Amine Methyl 4-vinylbenzoate monomers were co-polymerized with styrene and divinylbenzene to produce polystyrene beads having a substituted styrene of formula (I) (n=0, $R^1$=$CH_3$). One gram of the produced beads was suspended in 10 mL (10.6 gr, 100 mmol) neat, anhydrous, 2-(2-aminoethoxy) ethanol (Sigma-Aldrich Chemical) in a jacketed 100 ml round bottom flask with a 24/40 ground glass joint. The flask was stoppered using a rubber serum stopper which was secured using a zip tie. The flask was clamped to a wrist-action shaker and the jacketed flask was connected to a circulating heater containing ethylene glycol via silicon tubing. The tubing was secured using zip ties and the heater was warmed to 100° C.

The shaker was adjusted to give complete suspension and mixing of the beads in the ethylene diamine. The suspended beads were heated and shaken for 12 hours at 100° C. After 12 hours the heater was turned off and the flask allowed to cool to room temperature. The beads of formula (III) functionalized with terminal hydroxyl groups (n=0, Q=OH and p=1, q=1, r=0) were isolated by filtration in a sintered glass funnel and washed with 3×100 ml volumes of toluene, acetonitrile, and then ethyl ether. The filtration was kept under vacuum for 10 minutes after the final ether wash was completed to allow the beads to dry to a free-flowing state. The beads were then placed under high vacuum 170 mbar for 2 hr to remove all residual solvent.

Figure 7:
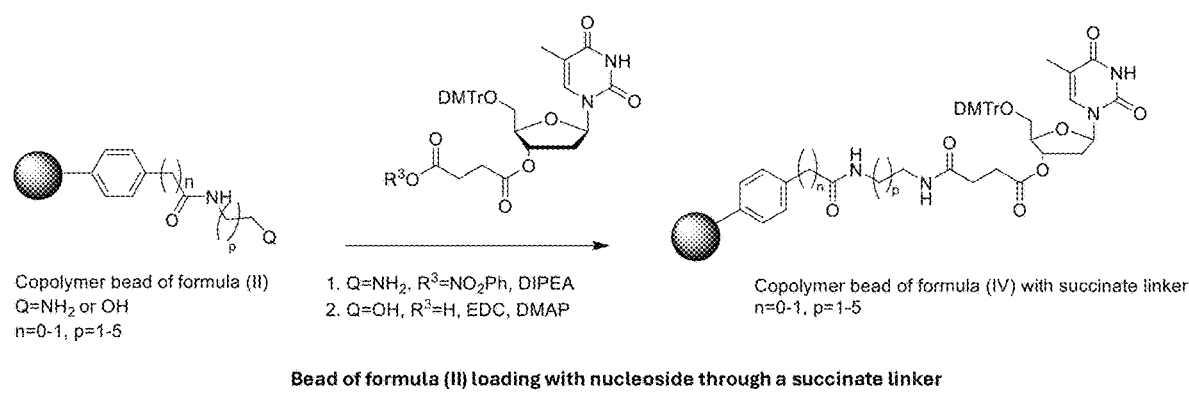
FIG. 7 is a schematic diagram showing loading of a bead of formula (II) with a nucleoside through a succinate linker, according to one embodiment.
Figure 9:
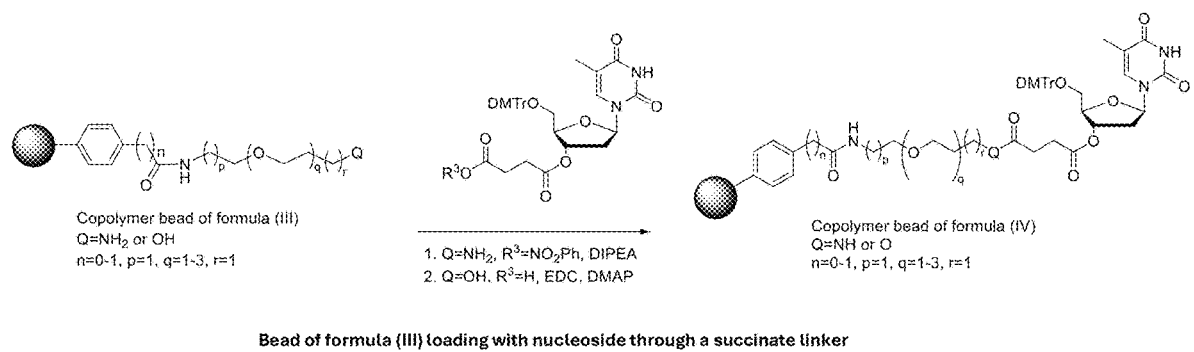
FIG. 9 is a schematic diagram showing loading of a bead of formula (III) with nucleoside through a succinate linker, according to one embodiment.

The hydroxyl groups were used to attach a protected nucleoside by reacting 50 mg of copolymer resin with 94 mg, 0.1 mmol of Thymidine, 5'-O-[bis(4-methoxyphenyl) phenylmethyl]-3'-[13-(2-cyanoethoxy)-15-methyl-14-(1-methylethyl)-4-oxo-12-oxa-5,14-diaza-13-phosphahexadecanoate] (ChemeGenes), dissolved in anhydrous acetonitrile at 0.1M in the presence of 0.1 M 5-(Ethylthio)-1H-tetrazole (Sigma-Aldrich) for 10 minutes at room temperature. The hydroxyl group loading was determined using an absorbance assay for the dimethoxytrityl protective group born on the 5'-hydroxyl of the thymidine nucleoside (see, e.g., FIGS. 7-9).

Example 6: Nucleoside Loading of the Copolymer Beads

I. Nucleoside Loading of the Amide/Amine Containing Beads Using a 3'-Nitrophenyl Succinate A dioxane solution was prepared by dissolving 766 mg, 1 mmol, thymidine, 5'-O-[bis(4-methoxyphenyl)phenylmethyl]-3'-(4-nitrophenyl butanedioate) (ChemGenes) in 10 mL of anhydrous dioxane giving a final concentration of 0.1M in a 50 ml round bottom flask with a 24/40 ground glass joint. One gram of the aminated beads comprising substituted styrenes of formula (II) and (III) prepared as described in Example 4 was suspended in the dioxane solution and 305 microliters of anhydrous N,N-diisopropylethylamine, 2 mmol, was added to the solution.

The flask was stoppered using a serum stopper and the flask clamped to a wrist-action shaker and shaken such that the beads were well suspended in the solution. The reaction was shaken for 12 hours at room temperature and then the beads were isolated in a sintered glass funnel. The beads were washed with 3×100 mL of dioxan, acetonitrile, and then ethyl ether. The filtration was kept under vacuum for 10 minutes after the final ether wash was completed to allow the beads to dry to a free-flowing state.

The beads were then dried under vacuum to remove the residual solvent. Nucleoside loading was determined using an absorbance assay for the dimethoxytrityl protective group born on the 5'-hydroxyl of the thymidine nucleoside. The results are shown in Table 2 below.

Beads of formula (IV) functionalized with a protected nucleoside through a cleavable succinate linker were successfully produced.

II. Nucleoside Loading of the Amide/Amine Containing Beads Using a 3'-Nucleoside Succinate An acetonitrile solution was prepared by dissolving 775 mg, 1 mmol, thymidine, 5'-O-[bis(4-methoxyphenyl)phenylmethyl]-3'-(hydrogen butanedioate) triethylamine salt (Hongene) in 10 mL of anhydrous acetonitrile giving a final concentration of 0.1M in a 50 ml round bottom flask with a 24/40 ground glass joint. One gram of the aminated beads comprising substituted styrene of formula (II) and (III) prepared as described in Example 4 was suspended in the acetonitrile solution, and 186 mg of N-(3-Dimethyl aminopropyl)-N'-ethylcarbodiimide (Sigma-Aldrich) added to the solution.

The flask was stoppered using a serum stopper and the flask clamped to a wrist-action shaker and shaken such that the beads were well suspended in the solution. The reaction was shaken for 12 hours at room temperature and then the beads were isolated in a sintered glass funnel. The beads were washed with 3×100 mL of acetonitrile, dichloromethane, and then ethyl ether. The filtration was kept under vacuum for 10 minutes after the final ether wash was completed to allow the beads to dry to a free-flowing state.

The beads were then dried under vacuum to remove the residual solvent. Nucleoside loading was determined using an absorbance assay for the dimethoxytrityl protective group born on the 5'-hydroxyl of the thymidine nucleoside (styrene of formula (II) (FIG. 7), styrene of formula (III) (FIG. 9), wherein DIPEA is N,N-diisopropylethylamine, EDC is 1-Ethyl-3-(3-dimethylaminopropyl) carbodiimide, and DMAP is 4-Dimethylaminopyridine).

Beads of formula (IV) functionalized with a protected nucleoside through a cleavable succinate linker were successfully produced.

III. Universal Linker Loading of the Amide/Hydroxyl Containing Beads

An acetonitrile solution was prepared by dissolving 779 mg, 1 mmol, 4-((6-(bis(4-methoxyphenyl)(phenyl) methoxy)-1,3-dioxo-2-phenyloctahydro-1H-4,7-epoxyisoindol-5-yl)oxy)-4-oxobutanoic acid triethylamine salt (ChemeGenes) in 10 mL of anhydrous acetonitrile giving a final concentration of 0.1M in a 50 ml round bottom flask with a 24/40 ground glass joint. One gram of the hydroxylated beads (Q=OH, n=0-1, p=1, q=0-1) comprising substituted styrenes of formula (II) and (III) prepared as described in Example 5 was suspended in the acetonitrile solution, and 186 mg of N-(3-Dimethyl aminopropyl)-N'-ethylcarbodiimide (Sigma-Aldrich) added to the solution.

The flask was stoppered using a serum stopper and the flask clamped to a wrist-action shaker and shaken such that the beads were well suspended in the solution. The reaction was shaken for 12 hours at room temperature and then the beads were isolated in a sintered glass funnel. The beads were washed with 3×100 mL of acetonitrile, dichloromethane, and then ethyl ether. The filtration was kept under vacuum for 10 minutes after the final ether wash was completed to allow the beads to dry to a free-flowing state.

Figure 10:
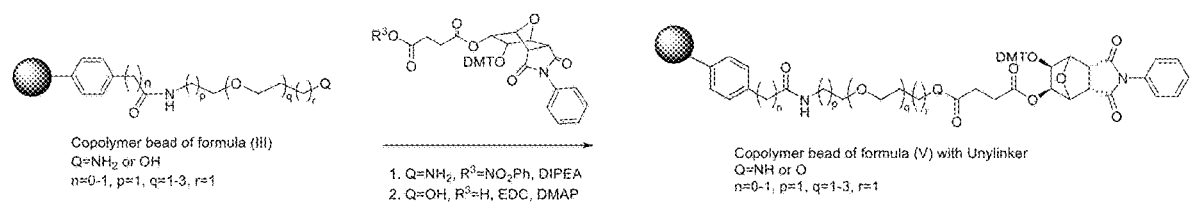
FIG. 10 is a schematic diagram showing universal cleavable linker loading of a bead of formula (III), according to one embodiment.

The beads were then placed under high vacuum 170 mbar for 2 hr to remove all residual solvent. Linker loading was determined using an absorbance assay for the dimethoxytrityl protective group born on a hydroxyl of the epoxyisoindole group of the universal linker (FIG. 10, wherein DIPEA is N,N-diisopropylethylamine, EDC is 1-Ethyl-3-(3-dimethylaminopropyl) carbodiimide, and DMAP is 4-Dimethylaminopyridine)

Beads functionalized with a cleavable linker were successfully produced.

IV. Nucleoside Loading of the Amide/Hydroxyl Containing Beads Using Thymidine-Succinyl Hexamide CED Phosphoramidite An acetonitrile solution was prepared by dissolving 1 gr, 1.06 mmol, 5'-O-[bis(4-methoxyphenyl)phenylmethyl]-3'-[13-(2-cyanoethoxy)-15-methyl-14-(1-methylethyl)-4-oxo-12-oxa-5,14-diaza-13-phosphahexadecanoate]-thymidine (ChemeGenes) in 10 mL of anhydrous acetonitrile in a 30 mL round bottom flask (0.1M) with a ground glass 24/40 joint. One gram of the amide/hydroxyl beads prepared as described in Example 5 was suspended in the acetonitrile solution. To the suspension of beads was added 260 gm of 5-(Ethylthio)-1H-tetrazole (Sigma-Aldrich).

The flask was sealed with a serum stopper and clamped to a wrist-action shaker. The reaction mixture was shaken for 1 hour at room temperature. The beads were isolated by filtration using a sintered glass funnel. The beads were washed with 3×100 mL of acetonitrile, dichloromethane, and then ethyl ether. The filtration was kept under vacuum for 10 minutes after the final ether wash was completed to allow the beads to dry to a free-flowing state.

The resulting beads were then placed under high vacuum 170 mbar for 2 hr to remove all residual solvent. Nucleoside loading was determined using an absorbance assay for the dimethoxytrityl protective group born on the 5'-hydroxyl of the thymidine nucleoside.

Copolymer beads functionalized with a 3'-succinate nucleoside through a phosphate linker as shown in FIG. 8 were successfully produced.

Example 7: Spectrophotometric Determination of Amine Loading Using Nitrophenyl Acetate The accessible amine loading of each copolymer bead of formula (II) or (III) was determined by reacting the aminated beads with 4-nitrophenyl acetate (Sigma-Aldrich) in anhydrous acetonitrile at a concentration of 2 millimolar, overnight in the presence of an equimolar amount of diisopropylethylamine. The evolution of the nitrophenoxide anion was measured by absorbance at 420 nm using an extinction coefficient of 5367.7 L/mol·cm, as compared to a blank solution allowed to react for an equal amount of time at the same concentration.

It was determined that amine loading on the copolymer beads was successful. The results are presented in Table 2 below. For example, the Proto-13 and Proto-23 formulations gave amine loading values of 419 and 474 µmol/g, respectively, when evaluated via spectrophotometric amine loading assay prior to loading of first nucleoside.

Example 8: Spectrophotometric Determination of Nucleoside Loading Using Absorbance of the 4,4'-Dimethoxytrityl Carbocation Nucleoside loading on copolymer beads of formula (IV) was determined by measuring the absorbance of the 4,4'-dimethoxytrityl cation in 0.1M toluene sulfonic acid monohydrate (Sigma Aldrich) in anhydrous acetonitrile (Sigma Aldrich) after its cleavage from the 5'-hydroxyl of the nucleoside attached to the bead. The copolymer beads (3 to 5 milligrams) were placed in a 100 mL volumetric flask and the toluene sulfonic acid solution added and shaken for 5 minutes. The nucleoside loading of the bead was determined by absorbance at 498 nm using an extinction coefficient of 70,000 L/mol·cm, as compared to a blank solution of 0.1M toluene sulfonic acid monohydrate.

It was determined that nucleoside loading on the copolymer beads was successful. The results are presented in Table 2 below.

Example 9: Small Scale DNA Synthesis on an ABI 394 Automated DNA Synthesizer

DNA synthesis was performed at a 1 micromole scale using an automated DNA synthesizer and phosphoramidite monomers. Fritted DNA synthesis columns (Glen Research) were loaded with the copolymer beads to 1 micromolar using the loading determined by the 4,4'-dimethoxytrityl cation assays. The beads were placed in the columns and a 23mer oligonucleotide was synthesized using the standard DNA synthesis parameters.

The phosphoramidite monomers (Glen Research, Chemgenes, Hongene) were dissolved in anhydrous acetonitrile at a standard concentration of 0.1M. Deblocking (detritylation) was performed using 3% (w/v) dichloroacetic acid in anhydrous toluene (Glen Research). Coupling was performed for 30 seconds using 0.25M 5-Ethylthio-1H-Tetrazole in Anhydrous Acetonitrile (Glen Research). Capping was performed prior to oxidation using 10% 1-Methylimidazole (w/v) in Tetrahydrofuran (Cap A) and Tetrahydrofuran/Pyridine/Acetic Anhydride (80:10:10, w/v, Cap B; Glen Research). Oxidation was performed using 0.02M Iodine in Tetrahydrofuran/Pyridine/Water (88:10:2, w/v; Glen Research).

After synthesis, the beads were placed in a sealed vial (ChemGlass) and cold concentrated ammonium hydroxide was added and allowed to react for 90 minutes at room temperature. After 90 minutes the vial was vortexed then placed in an ice bath to cool such that the ammonium hydroxide could be easily pipetted. Once cooled to 0° C. the supernatant was removed and transferred to another sealed vial. The vial was then heated overnight (12 hours) at 55° C. in a constant temperature heat block (VWR Scientific). The vial was once again placed in an ice bath and cooled to 0° C. for pipetting into a test tube. The ammonium hydroxide was removed under reduced pressure in a Speed-Vac concentrator (Thermo-Fisher). The resulting pellet was resuspended in water and analyzed using LC/MS, as described in Example 11.

Example 10: Large Scale DNA Synthesis on an Cytiva ATKA Synth Automated DNA Synthesizer Oligonucleotide synthesis studies were performed on a 400-480 micromole scale using an AKTA Oligosynt™ DNA/RNA synthesizer (Cytiva) and phosphoramidite monomers (Hongene). Synthesis columns, 11.45 mL with 2 cm bed height, were loaded with the polymer beads that swelled to 90% column volume in acetonitrile. A model, random sequence, 23mer modified oligonucleotide (5'-mA*fC*fA mAfCmA mGfGmA fAfAfA mGmUfA mAmUfA mCfCmG *mA*mA-3') was synthesized using typical DNA synthesis parameters.

Deblocking (detritylation) was performed using 10% (w/v) dichloroacetic acid in anhydrous toluene (Honeywell). The phosphoramidite monomers were dissolved in anhydrous acetonitrile at 0.2M. Coupling was performed by mixing the 3 equivalents of amidite with 0.5M 5-Ethylthio-1H-Tetrazole in anhydrous acetonitrile (Honeywell) and recycling for 7 minutes. Oxidation was performed using 0.05M iodine in pyridine/water (90:10 w/v; Glen Research) or 0.2M phenylacetyl disulfide (PADS) in acetonitrile/2,6-lutidine (1:1, v/v). Capping was performed using 20% 1-methylimidazole (v/v) in acetonitrile (Glen Research) and acetonitrile/2,6-lutidine/acetic anhydride (50:30:20, v/v; Glen Research).

After synthesis, the beads were dried under reduced pressure, mixed, and a 0.1 g sample was placed in a sealed vial (ChemGlass) and cold concentrated ammonium hydroxide was added and allowed to react for 20 hours at 36° C. The ammonium hydroxide was removed under reduced pressure in a SpeedVac vacuum concentrator (Thermo- Fisher). The resulting pellet was resuspended in water, filtered, and analyzed using LC/MS. The results are presented in Table 2 below.

Example 11: LC/MS Analysis of DNA/RNA Synthesis Products

Percent full length oligonucleotide product was determined via liquid chromatogram mass spectrometry (LC/MS) analysis of the crude synthesis products using a 6545 LC/Q-TOF system (Agilent).

The component buffer compositions were as follows. Buffer A: 92% Milli-Q H2O, 5% LC/MS grade MeOH, 0.245 M 1,1,1,3,3,3-hexafluoroisopropanol (HFIP), 18 mM triethylamine (TEA), and 2.5 uM ethylenediaminetetraacetic acid (EDTA); and Buffer B: 94% LC/MS grade MeOH, 2.5% Milli-Q H2O, 0.245 M HFIP, 18 mM TEA, and 2.5 uM EDTA.

Figure 11:
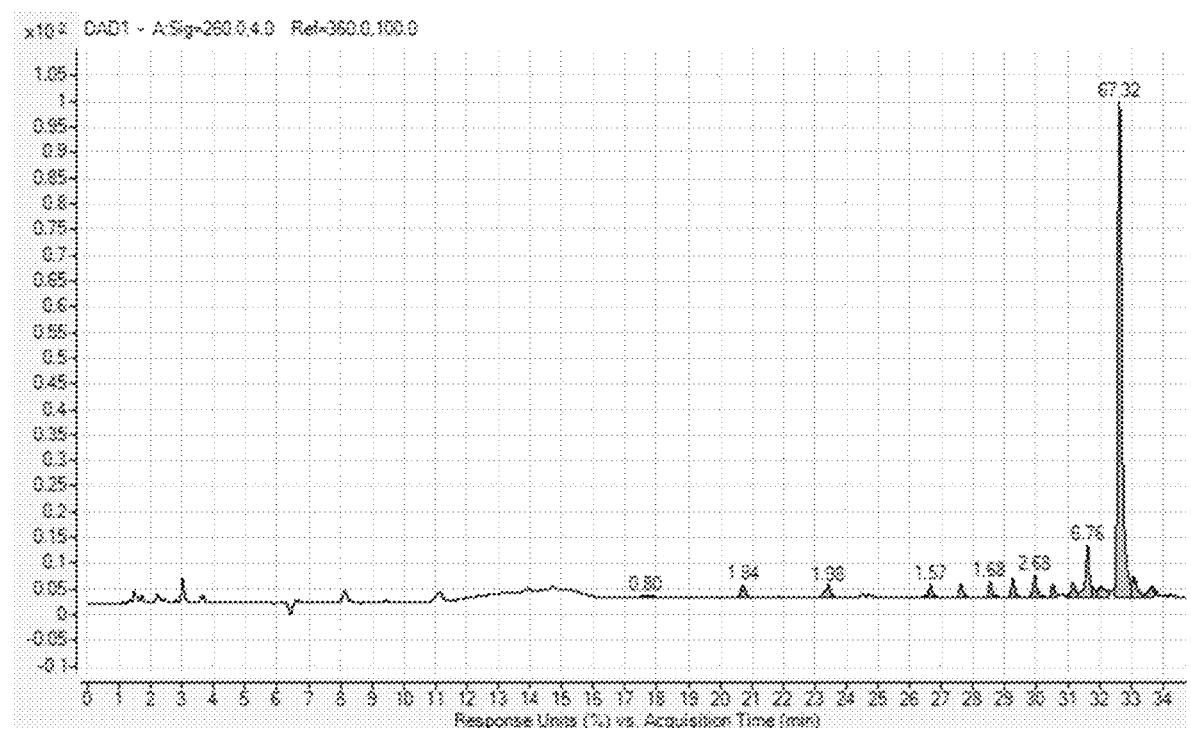
FIG. 11 is a graph showing liquid chromatography (LC) trace as determined by LC/mass spectrometry (MS) analysis of crude oligonucleotide synthesis products.

A reverse phase C18 analytical column (Waters Acquity, 1.7 μm, 2.1 mm×100 mm) was employed at a temperature of 60° C. A mobile phase gradient from 100% to 70% buffer A (0% to 30% buffer B) over 45 min was employed to analyze the crude synthesis products. The results are presented in Table 2 below. FIG. 11 is a graph showing liquid chromatography (LC) trace as determined by LC/mass spectrometry (MS) analysis of crude oligonucleotide synthesis products.

Results

Table 2 includes a summary of bead linker chemistries for various bead compositions, first nucleoside loading values (μmol per gram of resin), and the percent full length (FLP %) of 23mer oligonucleotide product synthesized with copolymer beads as disclosed herein. The results were obtained by LC/MS analysis of the crude product mixture.

For the results presented in Table 2, unless otherwise specified the target oligonucleotide was a DNA 23mer with a theoretical molecular weight of 7063.65 g/mol or a modified RNA 23mer with a theoretical molecular weight of 7698 g/mol. Nucleoside loading was determined via trityl assay and percent full length product was determined via LC/MS analysis, as previously described.

TABLE 2
Performance of various copolymer bead compositions, based on first nucleoside loading and percentage of 23-mer oligonucleotide (FLP)
| Bead Linker Chemistry | Descriptor | Nucleoside Loading (μmol/g) | FLP (%) |
|---|---|---|---|
| 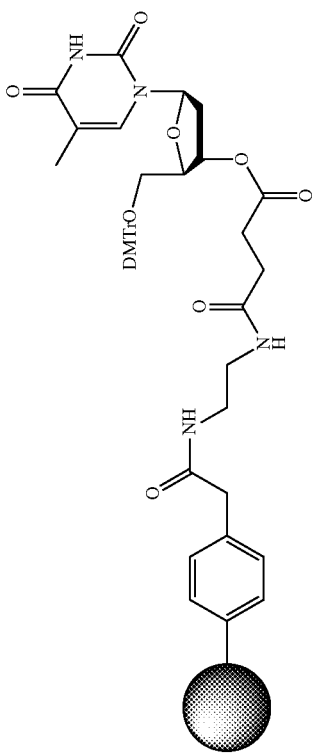 | Proto-13 | 308 | 49.5 |
| 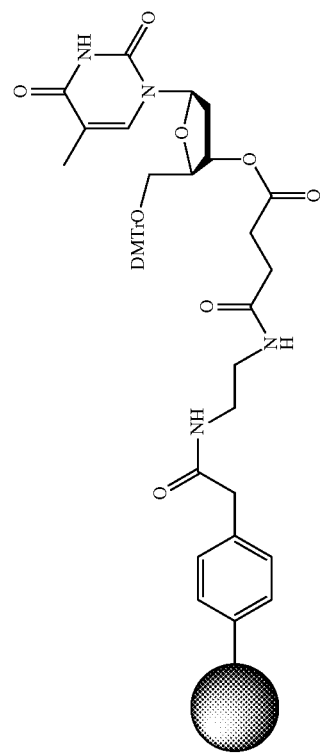 | Proto-23 | 350 | 52.3 |

TABLE 2-continued
Performance of various copolymer bead compositions, based on first nucleoside loading and percentage of 23-mer oligonucleotide (FLP)
| Bead Linker Chemistry | Descriptor | Nucleoside Loading (µmol/g) | FLP (%) |
|---|---|---|---|
| 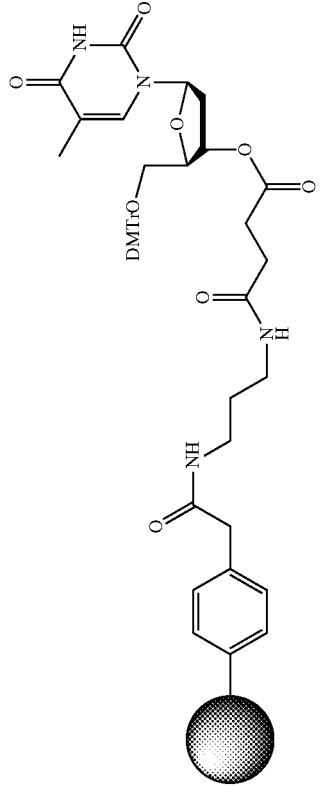 | Proto-23 | 333 | 42.3 |
| 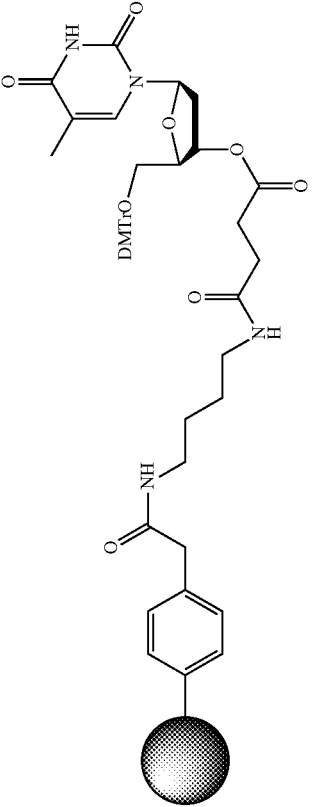 | Proto-23 | 309 | 48.5 |
| 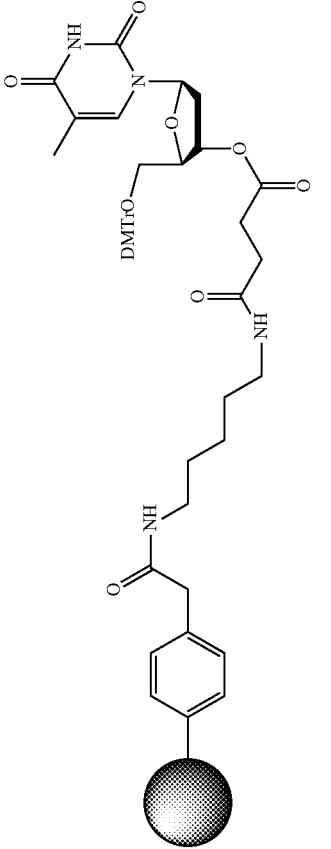 | Proto-23 | 338 | 43.4 |

TABLE 2-continued

Performance of various copolymer bead compositions, based on first nucleoside loading and percentage of 23-mer oligonucleotide (FLP)

| Bead Linker Chemistry | Descriptor | Nucleoside Loading (μmol/g) | FLP (%) |
|---|---|---|---|
| (structure: bead–C6H4–CH2–C(O)–NH–(CH2)6–NH–C(O)–CH2CH2–C(O)–O–[DMTrO-thymidine]) | Proto-23 | 250 | 51.9 |
| (structure: bead–C6H4–CH2–C(O)–NH–CH2CH2–O–CH2CH2–NH–C(O)–CH2CH2–C(O)–O–[DMTrO-thymidine]) | Proto-23 | 312 | 54.9 |

TABLE 2-continued
Performance of various copolymer bead compositions, based on first nucleoside loading and percentage of 23-mer oligonucleotide (FLP)
| Bead Linker Chemistry | Descriptor | Nucleoside Loading (µmol/g) | FLP (%) |
|---|---|---|---|
| 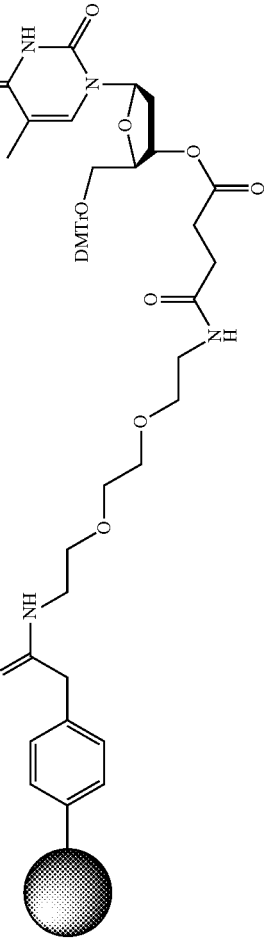 | Proto-23 | 311 | 58.4 |
| 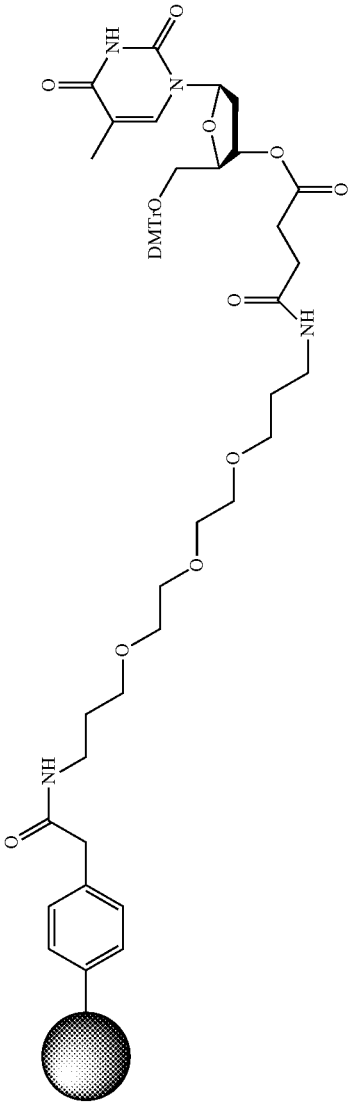 | Proto-23 | 135 | 67.4 |

TABLE 2-continued

Performance of various copolymer bead compositions, based on first nucleoside loading and percentage of 23-mer oligonucleotide (FLP)

| Bead Linker Chemistry | Descriptor | Nucleoside Loading (μmol/g) | FLP (%) |
|---|---|---|---|
| [structure] | Proto-23 | 440 | 35.6 |
| [structure] | Proto-23 | 424 | 59.6 |

TABLE 2-continued

Performance of various copolymer bead compositions, based on first nucleoside loading and percentage of 23-mer oligonucleotide (FLP)

| Bead Linker Chemistry | Descriptor | Nucleoside Loading (μmol/g) | FLP (%) |
|---|---|---|---|
| (structure) | Proto-23 | 417 | 43.3 |
| (structure) | Proto-23 | 364 | 41.0 |

TABLE 2-continued

Performance of various copolymer bead compositions, based on first nucleoside loading and percentage of 23-mer oligonucleotide (FLP)

| Bead Linker Chemistry | Descriptor | Nucleoside Loading (μmol/g) | FLP (%) |
|---|---|---|---|
| (structure) | Proto-23 | 357 | 40.2 |
| (structure) | Proto-23 | 396 | 50.4 |

TABLE 2-continued
Performance of various copolymer bead compositions, based on first nucleoside loading and percentage of 23-mer oligonucleotide (FLP)
| Bead Linker Chemistry | Descriptor | Nucleoside Loading (μmol/g) | FLP (%) |
|---|---|---|---|
|  | Proto-23 | 412 | 44.3 |
|  | Proto-23 | 340 | 44.2 |

TABLE 2-continued
Performance of various copolymer bead compositions, based on first nucleoside loading and percentage of 23-mer oligonucleotide (FLP)
| Bead Linker Chemistry | Descriptor | Nucleoside Loading (µmol/g) | FLP (%) |
|---|---|---|---|
| 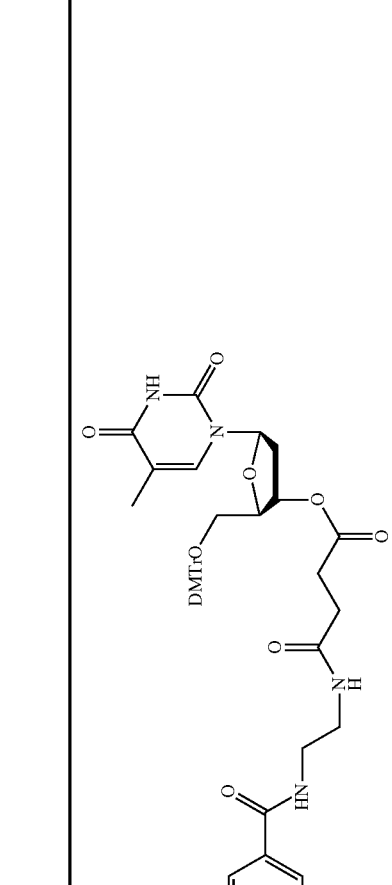 | Proto-13B | 205 | 52.75 |
| 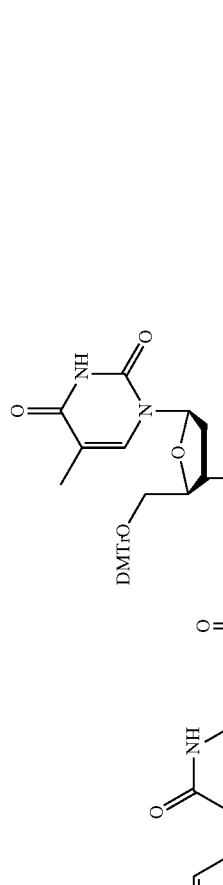 | Proto-X3 | 323 | 52.93 |

TABLE 2-continued
Performance of various copolymer bead compositions, based on first nucleoside loading and percentage of 23-mer oligonucleotide (FLP)
| Bead Linker Chemistry | Descriptor | Nucleoside Loading (µmol/g) | FLP (%) |
|---|---|---|---|
| 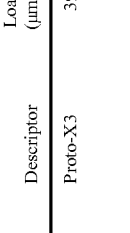 | Proto-X3 | 392 | 40.92 |
|  | Proto-13 | 451 | 68 |

TABLE 2-continued
Performance of various copolymer bead compositions, based on first nucleoside loading and percentage of 23-mer oligonucleotide (FLP)
| Bead Linker Chemistry | Descriptor | Nucleoside Loading (µmol/g) | FLP (%) |
|---|---|---|---|
| 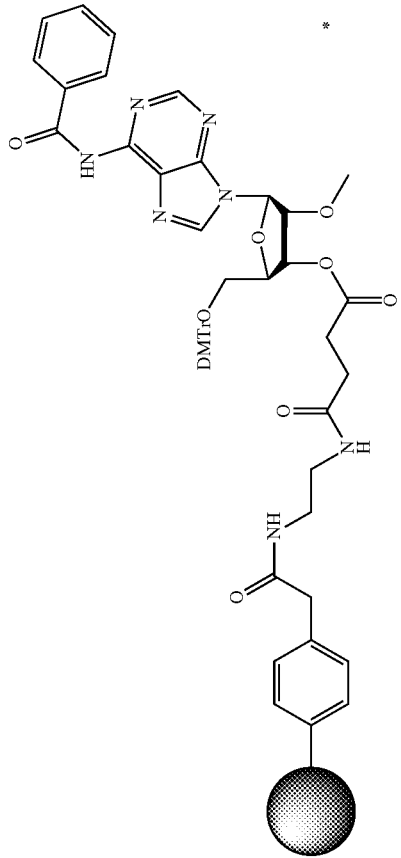 | Proto-13 | 282 | 69 |
| 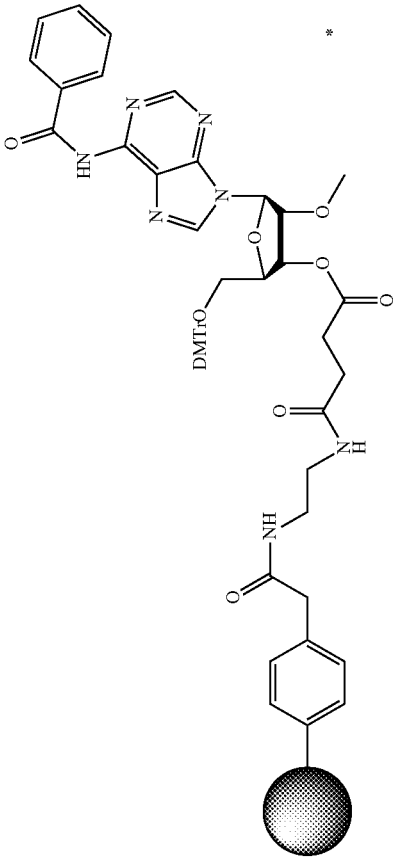 | Proto-23 | 290 | 68 |
*modified RNA 23mer The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure and are intended to be within the scope of the invention. Accordingly, the foregoing description and drawings are by way of example only.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed.

APPENDIX—EXEMPLARY SUBSTITUENTS

Alkoxy may refer to the group —O-alkyl. Alkoxy includes, by way of example, methoxy, ethoxy, n-propoxy, isopropoxy, n-butoxy, t-butoxy, sec-butoxy, and n-pentoxy.

Substituted alkoxy may refer to the group —O-(substituted alkyl).

Acyl may refer to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—. Acyl may include the acetyl group $CH_3C(O)$—.

Acylamino may refer to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl.

Acyloxy may refer to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—.

Amino may refer to the group —$NH_2$.

Substituted amino may refer to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

Aminocarbonyl may refer to the group —C(O) NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group.

Aminothiocarbonyl may refer to the group —C(S) NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group.

Aminocarbonylamino may refer to the group —NRC(O) NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group.

Aminothiocarbonylamino may refer to the group —NRC(S) NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group.

Aminocarbonyloxy may refer to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group.

Aminosulfonyl may refer to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group.

Aminosulfonyloxy may refer to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group.

Aminosulfonylamino may refer to the group —NR—SO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where R' and R" are optionally joined together with the nitrogen bound thereto to form a heterocyclic or substituted heterocyclic group.

Amidino may refer to the group —C(=NR")R'R'" where R', R", and R'" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group.

Aryloxy may refer to the group —O-aryl, and includes, by way of example, phenoxy and naphthoxy.

Substituted aryloxy may refer to the group —O-(substituted aryl).

Arylthio may refer to the group —S-aryl.

Substituted arylthiol may refer to the group —S-(substituted aryl).

Alkenyl may refer to alkenyl groups having carbon atoms, e.g., 2 to 6, 2 to 4, or more carbon atoms, and having at least 1 or from 1 to 2 sites of alkenyl unsaturation. Such groups are exemplified, for example, by vinyl, allyl, and but-3-en-1-yl.

Substituted alkenyl may refer to alkenyl groups having substituents, e.g., 1 to 3, 1 to 2, or more substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, with the proviso that any hydroxy substitution is not attached to a vinyl (unsaturated) carbon atom.

Alkynyl may refer to alkynyl groups having carbon atoms, e.g., 2 to 6, 2 to 4, or more carbon atoms and having at least 1 or from 1 to 2 sites of alkynyl unsaturation.

Substituted alkynyl may refers to alkynyl groups having substituents, e.g., 1 to 3, 1 to 2, or more substituents. Exemplary substituents are selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, with the proviso that any hydroxy substitution is not attached to an acetylenic carbon atom.

Carbonyl may refer to the divalent group —C(O)— which is equivalent to —C(=O)—.

Carboxyl or carboxy may refer to —COOH or salts thereof.

Carboxyl ester or carboxy ester may refer to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, (Carboxyl ester)amino may refer to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen.

(Carboxyl ester)oxy may refer to the group —O—C(O) O-alkyl, substituted-O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic.

Cyano may refer to the group —CN.

Cycloalkyl may refer to cyclic alkyl groups of from 3 to 10 (or more) carbon atoms having single or multiple cyclic rings including fused, bridged, and spiro ring systems. Examples of cycloalkyl groups include, for instance, adamantyl, cyclopropyl, cyclobutyl, cyclopentyl, and cyclooctyl.

Cycloalkenyl may refer to non-aromatic cyclic alkyl groups of from 3 to 10 (or more) carbon atoms having single or multiple cyclic rings and having at least one >C=C< ring unsaturation, e.g., from 1 to 2 sites of >C=C< ring unsaturation.

Substituted cycloalkyl and substituted cycloalkenyl may refer to a cycloalkyl or cycloalkenyl group having substituents, e.g., 1 to 5, 1 to 3, 1 to 2, or more substituents. Exemplary substituents are selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio.

Cycloalkyloxy may refer to —O-cycloalkyl.

Substituted cycloalkyloxy may refer to —O-(substituted cycloalkyl).

Cycloalkylthio may refer to —S-cycloalkyl.

Substituted cycloalkylthio may refer to —S-(substituted cycloalkyl).

Cycloalkenyloxy may refer to —O-cycloalkenyl.

Substituted cycloalkenyloxy may refer to —O-(substituted cycloalkenyl).

Cycloalkenylthio may refer to —S-cycloalkenyl.

Substituted cycloalkenylthio may refer to —S-(substituted cycloalkenyl).

Guanidino may refer to the group —NHC(=NH)NH$_2$.

Substituted guanidino may refer to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen.

H may refer to hydrogen.

Halo or halogen may refer to fluoro, chloro, bromo and iodo.

Hydroxy or hydroxyl may refer to the group —OH.

Heteroaryl may refer to an aromatic group of carbon atoms, e.g. 1 to 10 (or more) carbon atoms, and heteroatoms, e.g., 1 to 4 (or more) heteroatoms, selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Exemplary heteroaryls include pyridinyl, pyrrolyl, indolyl, thiophenyl, and furanyl.

Substituted heteroaryl may refer to heteroaryl groups that are substituted, e.g., 1 to 5, 1 to 3, 1 to 2 or more substituents. Exemplary substituents are selected from the group consisting of the same group of substituents defined for substituted aryl.

Heteroaryloxy may refer to —O-heteroaryl.

Substituted heteroaryloxy may refer to the group —O-(substituted heteroaryl),

Heteroarylthio may refer to the group —S-heteroaryl.

Substituted heteroarylthio may refer to the group —S-(substituted heteroaryl).

Heterocycle or heterocyclic or heterocycloalkyl or heterocyclyl may refer to a saturated or unsaturated group having a single ring or multiple condensed rings, including fused bridged and spiro ring systems, carbon atoms, e.g., 1 to 10 (or more) carbon atoms, and from hetero atoms, e.g., 1 to 4 hetero atoms (or more), selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

Substituted heterocyclic or substituted heterocycloalkyl or substituted heterocyclyl may refer to heterocyclyl groups that are substituted, e.g., with 1 to 5, 1 to 3, 1 to 2 or more, of the same substituents as defined for substituted cycloalkyl.

Heterocyclyloxy may refer to the group —O-heterocycyl.

Substituted heterocyclyloxy may refer to the group —O-(substituted heterocycyl).

Heterocyclylthio may refer to the group —S-heterocycyl,

Substituted heterocyclylthio may refer to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

Nitro may refer to the group —NO$_2$.

Oxo may refer to the atom (═O) or (—O$^-$).

Sulfonyl may refer to the divalent group —S(O)$_2$—.

Substituted sulfonyl may refer to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic. Substituted sulfonyl may include groups such as methyl-SO$_2$—, phenyl-SO$_2$—, and 4-methylphenyl-SO$_2$—.

Sulfonyloxy may refer to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic.

Thioacyl may refer to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—.

Thiol may refer to the group —SH.

Thiocarbonyl may refer to the divalent group —C(S)— which is equivalent to —C(═S)—.

Thione may refer to the atom (═S).

Alkylthio may refer to the group —S-alkyl.

Substituted alkylthio may refer to the group —S-(substituted alkyl),

The invention claimed is:

1. A copolymer bead comprising a first repeating motif, a second repeating motif being a compound of one of formulas (II) or (III), and a crosslinking agent comprising a divinyl compound,

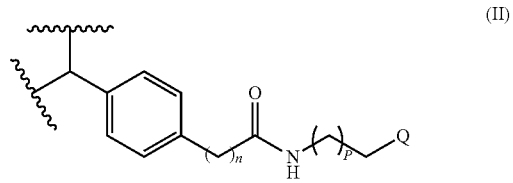

wherein Q is NH$_2$ or OH, n is an integer from 0 to 12, and p is an integer from 0 to 11;

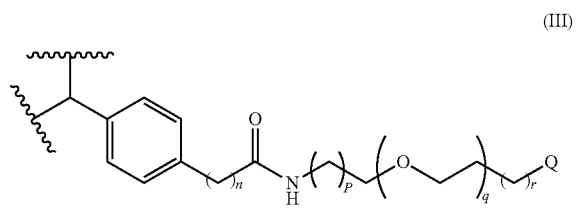

wherein Q is NH$_2$ or OH, n is an integer from 0 to 12, p and r are integers each independently from 0 to 11, and q is an integer from 0 to 6.

2. The copolymer bead of claim 1, wherein the first repeating motif comprises a styrene.

3. The copolymer bead of claim 1, wherein the divinyl compound comprises divinylbenzene or ethylene glycol di(meth)acrylate.

4. The copolymer bead of claim 1, having a bead diameter between 30 and 200 μm.

5. The copolymer bead of claim 4, having a bead diameter between 50 and 90 μm.

6. The copolymer bead of claim 1, further comprising at least one of a cleavable linker, a nucleoside or nucleoside derivative bound to the second repeating motif at the terminal amine or hydroxyl functional group.

7. The copolymer bead of claim 6, wherein the second repeating motif and nucleoside derivative are represented by formula (IV):

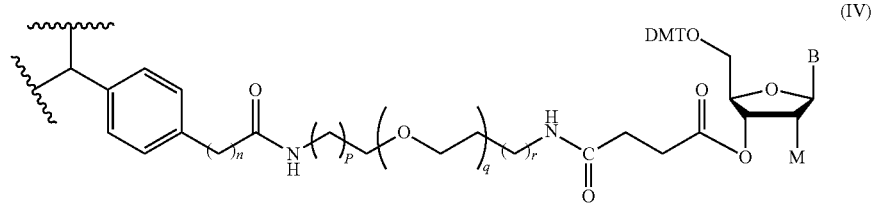

wherein n is 0 or 1; p is 1-6; q is 0-3; r is 1-6; B is a nucleobase, a protected nucleobase, a nucleobase analog, or a protected nucleobase analog; M is H, a protected hydroxyl, O-alkyl, 2-methoxyethanolate (MOE), F, or a methylene linked to C4' of the ribose.

8. The copolymer bead of claim 6, wherein the second repeating motif and cleavable linker are represented by formula (V):

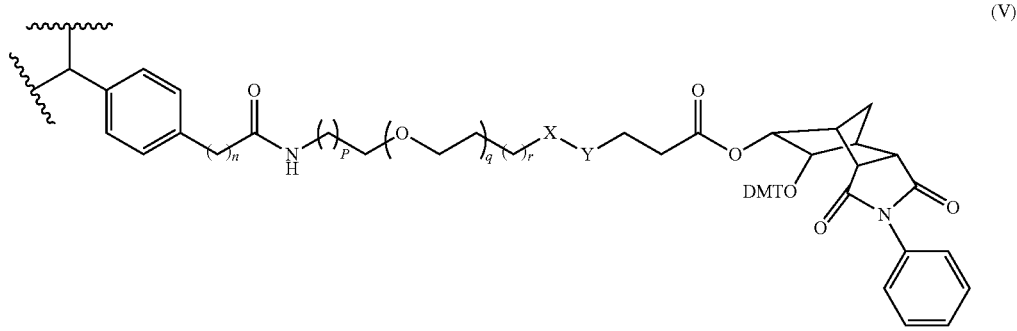

(V)

wherein n is 0 or 1, p is 1-6, q is 0-3, r is 1-6, X is NH or O, and Y is C=O.

9. The copolymer bead of claim 1, having a porous structure.

10. A resin formed of copolymer beads comprising a first repeating motif, a second repeating motif having a substituted styrene with an ester functional group or an amide with a terminal amine or hydroxyl functional group, and a cross-linking agent comprising a divinyl compound, the copolymer beads being capable of expanding to a predetermined volume substantially uniformly in polar and non-polar solvents, the predetermined volume being from about 2 to about 3 times their dry volume.

11. The resin of claim 10, wherein the second repeating motif comprises a substituted styrene of formula (I),

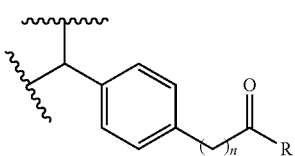

(I)

wherein n is an integer between 0 and 12; R is O—$R^1$ or NH—$R^2$-Q; $R^1$ is a $C_1$-$C_6$ alkyl, a $C_1$-$C_6$ substituted alkyl, a $C_6$-$C_{12}$ aryl or a $C_6$-$C_{12}$ substituted aryl; $R^2$ is a $C_1$-$C_{36}$ alkyl or a $C_1$-$C_{36}$ substituted alkyl, and Q is $NH_2$ or OH.

12. The resin of claim 11, wherein the second repeating motif is a substituted styrene of formula (I), wherein n is 1 and $R^1$ is methyl.

13. The resin of claim 10, wherein the first repeating motif comprises a styrene.

14. The resin of claim 10, wherein the divinyl compound comprises divinylbenzene, ethylene glycol di(meth)acrylate, or a combination thereof.

15. The resin of claim 10, wherein the copolymer beads have an average bead diameter between 30 and 200 μm.

16. The resin of claim 15, wherein the copolymer beads have an average bead diameter between 50 and 90 μm.

17. The resin of claim 10, wherein the second repeating motif is a compound of one of formulas (II) or (III):

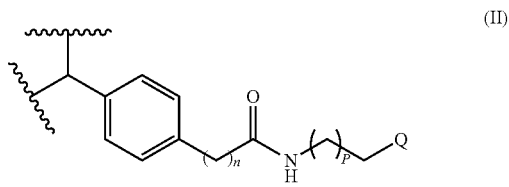

(II)

wherein Q is $NH_2$ or OH, n is an integer from 0 to 12, and p is an integer from 0 to 11;

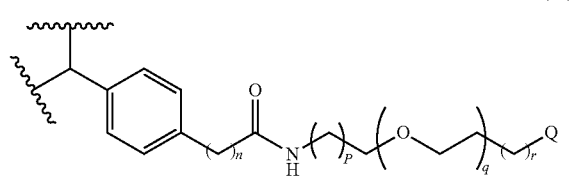

(III)

wherein Q is $NH_2$ or OH, n is an integer from 0 to 12, p and r are integers each independently from 0 to 11, and q is an integer from 0 to 6.

18. The resin of claim 10, wherein the copolymer beads have a porous structure.

* * * * *